United States Patent
Hammerman

(10) Patent No.: US 8,709,400 B2
(45) Date of Patent: Apr. 29, 2014

(54) INDUCEMENT OF ORGANOGENETIC TOLERANCE FOR PANCREATIC XENOTRANSPLANT

(75) Inventor: Marc Hammerman, St. Louis, MO (US)

(73) Assignee: Washington University, St. Louis, MO (US)

( * ) Notice: Subject to any disclaimer, the term of this patent is extended or adjusted under 35 U.S.C. 154(b) by 437 days.

(21) Appl. No.: 12/843,796

(22) Filed: Jul. 26, 2010

(65) Prior Publication Data

US 2011/0020294 A1 Jan. 27, 2011

Related U.S. Application Data

(60) Provisional application No. 61/228,822, filed on Jul. 27, 2009.

(51) Int. Cl.
*C12N 5/00* (2006.01)

(52) U.S. Cl.
USPC .......................................... 424/93.7; 435/325

(58) Field of Classification Search
None
See application file for complete search history.

(56) References Cited

U.S. PATENT DOCUMENTS

| | | | |
|---|---|---|---|
| 5,593,673 A | 1/1997 | Dinsmore | |
| 5,725,854 A * | 3/1998 | Selawry | 424/93.7 |
| 5,879,939 A * | 3/1999 | Gray et al. | 435/379 |
| 5,976,524 A | 11/1999 | Hammerman | |
| 6,008,241 A * | 12/1999 | Chan et al. | 514/410 |
| 6,436,704 B1 * | 8/2002 | Roberts et al. | 435/366 |
| 7,074,762 B2 | 7/2006 | Hammerman | |
| 7,384,630 B2 | 6/2008 | Hammerman | |
| 2004/0001801 A1 * | 1/2004 | Madison et al. | 424/85.1 |
| 2004/0136971 A1 * | 7/2004 | Scharp et al. | 424/93.7 |
| 2004/0197375 A1 * | 10/2004 | Rezania et al. | 424/426 |
| 2008/0267926 A1 * | 10/2008 | Martinson et al. | 424/93.7 |

FOREIGN PATENT DOCUMENTS

| | | |
|---|---|---|
| EP | 0853942 | 8/2005 |
| WO | WO 00/41713 | 7/2000 |
| WO | WO 00/61605 | 10/2000 |
| WO | WO 02/069703 | 9/2002 |
| WO | WO 03/083064 | 10/2003 |

OTHER PUBLICATIONS

Carlsson GL et al. 2010. Immunohistochemistry of pancreatic development in cattle and pig. Anat Histol Embryol 39: 107-19. Abstract only.*
Faustman DL et al. 1984. Prevention of rejection of murine islet allografts by pretreatment with anti-dendritic cell antibogy. Proc Natl Acad Sci USA 81: 3864-3868.*
Lafferty K et al. 1983. Immunobiology of tissue transplantation: a return to the passenger leukocyte concept. Ann Rev Immunol 1: 143-173.*
Wilson JD et al. 1989. Role of CD4+ T-lymphocytes in rejection by mice of fetal pig proislet xenografts. Diabetes 38 (Suppl. 1): 217-219.*
Abraham et al., Human pancreatic islet-derived progenitor cell engraftment in immunocompetent mice, Am. J. Pathology, 2004, 164(3), 817-830.
Adams et al., Regimens of IGF-I treatment in fetal pancreas transplantation, J Surgical Res, 1997, 68:73-78.
Armstrong et al., Establishment of metanephros transplantation in mice highlights contributions by both nephrectomy and pregnancy to developmental progression, Experimental Nephrology, 2005, 101(4):e155-e164.
Burkly et al., Tolerance in transgenic mice expressing major histocompatibility molecules extrathymically on pancreatic cells, Science, 1990, 248(4961):1364-1368.
Cantarovich et al., Rapid failure of pig islet transplantation in non human primates, Xenotransplantation, 2002, 9:25-35.
Cardona et al., Long-term survival of neonatal porcine islets in non-human primates by targeting costimulation pathways, Nature Medicine, 2006, 12:304-306.
Casu et al., Metabolic aspects of pig-to-monkey (*Macaca fascicularis*) islet transplantation: Implications for translation into clinical practice, Diabetologia, 2008, 51:120-129.
Cirulli et al., Expression of neural cell adhesion molecule (N-CAM) in rat islets and its role in islet type segregation, J. Cell Sci., 1994, 107(6): 1429-1436.
Contreras, Extrahepatic transplant sites for islet xenotransplantation, Xenotransplantation, 2008, 15:99-101.
Crispe, Hepatic T cells and liver tolerance, Nature Reviews Immunology, 2003, 3:51-62.
Crnic et al., Loss of neural cell adhesion molecule induces tumor metastasis by p-regulating lymphangiogenesis, Cancer Res., 2004, 64(23):8630-8638.
Dufrane et al., Six-month survival of microencapsulated pig islets and alginate biocompatibility in primates: proof of concept, Transplantation, 2006, 81:1345-1353.
Edamura et al., Effect of long term culture on the expression of antigens and adhesion molecule in single porcine pancreatic endocrine cells, Xenotransplantation, 2005, 12(4):327-332.
Eventov-Friedman et al., Embryonic pig pancreatic tissue transplantation for the treatment of diabetes, PLoS Medicine, 2006, 3(7):1165-1177.
Groth et al., Xenoislet transplantation: experimental and clinical aspects, J Mol Med, 1999, 77:153-154.
Gunawardana et al., Subcutaneous transplantation of embryonic pancreas for correction of type 1 diabetes, Am J Physiol Endocrinol Metab, 2008, 296:E323-E332.
Hamamoto et al., Recovery of function and mass of endogenous beta-cells in streptozotocin-induced diabetic rats treated with islet transplantation, Biochem Biophys Res Commun, 2001, 287:104-109.

(Continued)

*Primary Examiner* — Lora E Barnhart Driscoll
(74) *Attorney, Agent, or Firm* — Dentons US LLP

(57) ABSTRACT

Provided herein is an approach to establish organogenetic tolerance via prior transplantation of pig embryonic pancreas, thereby enabling subsequent implantation of porcine islets in a subject without the need for immune-suppression. In one aspect of the invention, porcine pancreatic primordia are implanted into a mammalian subject, and after a period of time sufficient to induce tolerance, porcine islet cells are implanted in the subject.

22 Claims, 19 Drawing Sheets

(56) References Cited

OTHER PUBLICATIONS

Hammerman, Interaction of insulin with the renal proximal tubular cell, Am J Physiol, 1985, 249:F1-F11.
Hammerman, Organogenesis of endocrine pancreas from transplanted embryonic anlagen, Transplant Immunology, 2004, 12(3-4):249-258.
Hammerman, Organogenesis of kidneys following transplantation of renal progenitor cells, Transplant Immunology, 2004, 12(3-4):229-239.
Hammerman, Transplantation of renal primordia: Renal organogenesis, Pediatric Nephrology, 2007, 22(12):1991-1998.
Hammerman, Treatment for end-stage renal disease: An organogenesis/tissue engineering odyssey, Transplant Immunology, 2004, 12:211-218.
Hammerman, Windows of opportunity for organogenesis, Transplant Immunology, 2005, 15(1): 1-8.
Hering and Walawalkar, Pig-to-nonhuman primate isle xenotransplantation, Transplant Immunology, 2009, 21:81-86.
Hering et al., Prolonged diabetes reversal after intraportal xenotransplantation of wild-type porcine islets in immunosuppressed nonhuman primates, Nature Medicine, 2006, 12:301-303.
Ibrahim et al., Selected physiologic compatibilities and incompatibilities between human and porcine organ systems, Xenotransplantation, 2006, 13(6): 488-499.
Jansen et al., An immunohistochemical study on organized lymphoid cell infiltrates in fetal and neonatal pancreases. A comparison with similar infiltrates found in the pancreas of a diabetic infant, Autoimmunity, 1993, 15:31-38.
Kallskog et al. Lymphatic vessels in pancreatic islets implanted under the renal capsule of rats, Am J Transplant, 2006, 6:680-686.
Kim et al., Intercellular signals regulating pancreas development and function, Genes & Development, 2001, 15(2):111-127.
Komoda et al. Survival of adult islet grafts from transgenic pigs with N-acetylglucosaminyltransferase-III (GnT-III) in cynomolgus monkeys, Xenotransplantation, 2005, 12:209-216.
Korsgren, Acute cellular xenograft rejection, Xenotransplantation, 1997, 4:11-19.
MacPherson and Smith, Mesenteric lymph nodes at the center of immune anatomy, J Experimental Medicine, 1997, 203:497-500.
Markmann et al., Antigen presenting function of class II MHC expressing pancreatic beta cells, Nature, 1988, 336(6198):476-479.
Marshall et al., Increasing renal mass improves survival in anephric rats following metanephros transplantation, Exp Physiol, 2007, 92(1):263-271.
Matsunaga and Rahman, In search of the origin of the thymus: the thymus and GALT may be evolutionarily related, Scand J Immunol, 2001, 53:1-6.
Murray et al., Neonatal porcine islet cells induce humanCD4+ but not CD8+ lymphocyte proliferation and resist cell-mediated cytolytic injury in vitro, Diabetes, 1999, 48(3):1713-1719.
Peterson et al., Zucker diabetic fatty rat as a model for non-insulin-dependent diabetes, ILAR News, 1990, 32(3):16-19.
Phillips et al., Leptin receptor missense mutation in the fatty zucker rat, Nat. Genetics, 1996, 13(1):18-19.
Porta et al., Tolerance and M2 (alternative) macrophage polarization are related processes orchestrated by p50 nuclear factor kappaB, Proc Natl Acad Sci USA, 2009, 106:14978-83.
Rogers et al., Glucose tolerance normalization following transplantation of pig pancreatic primordia into non-immunosuppressed diabetic ZDF rats, Transplant Immunology, 2006, 16:176-184.
Rogers et al., Incubation of metanephroi with vitamin D increases numbers of glomeruli, Organogenesis, 2004, 1(2):52-54.
Rogers et al., Intraperitoneal transplantation of pancreatic anlagen, ASAIO Journal, 2003, 49:527-532.
Rogers et al., Islet cell engraftment and control of diabetes in rats following transplantation of pig pancreatic anlagen, Am. J. Physiol, 2004, 286:E502-E509.
Rogers et al., Long-term engraftment following transplantation of pig pangreatic primordia into non-immunosuppressed diabetic rhesus macaques, Xenotransplantation, 2007, 14:591-602.
Rogers et al., Normalization of glucose post-transplantation into diabetic rats of pig pancreatic primordia preserved in vitro, Organogenesis, 2008, 4:48-51.
Rogers et al., Normalization of glucose post-transplantation of pig pancreatic anlagen into non-immunosuppressed diabetic rats depends on obtaining anlagen prior to embryonic day 35, Transplant Immunology, 2005, 14:67-75.
Rogers et al., Prolongation of life in anephric rats following de novo renal organogenesis, Organogenesis, 2004, 1(1):22-25.
Rogers et al., Transplantation of developing metanephroi into adult rats, Kidney Int, 1998, 54:27-37.
Rogers, Engraftment of cells from porcine islets of Langerhans and normalization of glucose tolerance following transplantation of pig pancreatic primordia in nonimmune-suppressed diabetic rats, Am. J. Pathol., 2010, 177:854-864.
Rosines et al., Staged in vitro reconstitution and implantation of engineered rat kidney tissue, Proc. Natl. Acad. Sci USA, 2007, 104(52)20938-20943.
Rubbia-Brandt et al., Lymphatic vessel density and vascular endothelial growth factor-C expression correlate with malignant behavior in human pancreatic endocrine tumors, Clin. Cancer Research, 2004, 10(20)6919-6928.
Schroeder et al., Tolerance and the "Holy Grail" of transplantation, J Surgical Research, 2003, 111:109-119.
Sipos et al., Expression of lymphangiogenic factors and evidence of intratumoral lymphangiogenesis in pancreatic endocrine tumors, American Journal of Pathology, 2004, 165(4):1187-1197.
Swanson et al. Improved methods for the isolation and purification of porcine islets, Human Immunology, 2001, 62:739-749.
Takeda et al., Differential origin for endothelial and mesangial cells after transplantation of pig fetal renal primordia into rat, Transplant Immunology, 2006, 15(3):211-215.
Turley et al., Endocrine self and gut non-self intersect in the pancreatic lymph nodes, Proc Natl Acad Sci USA, 2005, 102:17729-17733.
Whitworth et al. Method of oocyte activation affects cloning efficiency in pigs, Molecular Reproduction & Development, 2009, 76:490-500.
Williams, Minireview: Finding the sweet spot: Peripheral versus central glucagon-like peptide 1 action in feeding and glucose homeostasis, Endocrinolgy, 2009, 150:2997-3001.
Worbs et al. Oral tolerance originates in the intestinal immune system and relies on antigen carriage by dendritic cells, J Experimental Medicine, 2006, 203:519-527.
Yokoo et al., Human mesenchymal stem cells in rodent whole embryo culture are reprogrammed to contribute to kidney tissues, Proc. Natl. Acad. Sci., 2005, 102(9):3296-3300.
Yokoo et al., Xenobiotic kidney organogenesis from human mesenchymal stem cells using a growing rodent embryo, J. Am. Soc. Nephrol, 2006, 17(4):1026-1034.
Youson and Al-Mahrouki, Ontogenetic and phylogenetic development of the endocrine pancreas (islet organ) in fish, General and Comparative Endocrinology, 1999, 116:303-335.
GenBank Accession No. AY044828, submission dated Jul. 2002, last accessed Nov. 2010; 12 pages.
GenBank Accession No. AY609582, submission dated Jan. 2005, last accessed Nov. 2010; 2 pages.
GenBank Accession No. XM_001093871, submission dated Jun. 2010, last accessed Nov. 2010; 2 pages.
GenBank Accession No. XP_001093871, submission dated Jun. 2010, last accessed Nov. 2010; 2 pages.

* cited by examiner

INDUCEMENT OF ORGANOGENETIC TOLERANCE FOR PANCREATIC XENOTRANSPLANT

CROSS-REFERENCE TO RELATED APPLICATIONS

This application claims priority from U.S. Provisional Application Ser. No. 61/228,822 filed on Jul. 27, 2009, which is incorporated herein by reference in its entirety.

STATEMENT REGARDING FEDERALLY SPONSORED RESEARCH OR DEVELOPMENT

This invention was made in part with Government support under P30 DK079333. The Government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present invention generally relates to xenotransplant-based treatment of pancreatic disorders, such as diabetes mellitus.

BACKGROUND

Transplantation therapy for human diabetes is limited by a shortage of donor organs, and outcomes are complicated by immunosuppression. While porcine pancreas is a candidate for organ donation, the severity of humoral rejection effectively precludes the use of pigs as whole pancreas donors in non-human primates or humans. Isolated islets of Langerhans (islets), like most other cell transplants, can be transplanted into non-human primates or humans without initiating humoral rejection. But sustained insulin independence from, for example, pig to primate islet or neonatal islet transplantation, can be achieved only through the use of immune-suppressive agents that are not approved for human use or would result in an unacceptable level of morbidity in humans (see e.g., Hering et al. 2006 Nature Medicine 12, 301-303; Cardona et al. 2006 Nature Medicine 12: 304-306; Schroeder 2003 Journal of Surgical Research 111, 109-119).

Xenotransplantation in host mesentery of pig pancreatic primordia obtained very early during organogenesis (e.g., embryonic day 28 (E28)) can obviate the need for immune-suppression in rat or rhesus macaques (see Rogers et al. 2004 Am. J. Physiol. 286, E502-E509; Rogers et al. 2005 Transplant Immunology 14: 67-75; Rogers et al. 2006 Transplant Immunology 16, 176-184; Rogers and Hammerman 2008 Organogenesis 4, 48-51; Rogers et al. 2007 Xenotransplantation 14, 591-602). Glucose tolerance can be normalized in streptozotocin (STZ)-diabetic (type 1) Lewis rats or ZDF (type 2) diabetic rats via transplantation in mesentery of pig pancreatic primordia obtained very early during embryogenesis (on embryonic day 28 (E28)—just after the organ differentiates and prior to the time dorsal and ventral anlagen fuse) without host immune-suppression (see Rogers et al. 2004 Am. J. Physiol. 286, E502-E509; Rogers et al. 2005 Transplant Immunology 14: 67-75; Rogers et al. 2006 Transplant Immunology 16, 176-184; Rogers and Hammerman 2008 Organogenesis 4, 48-51). No rat insulin was reported to be detected in STZ-treated rats. Rather porcine insulin circulates post-transplantation of E28 pig pancreatic primordia (embryonic pancreas) and levels increase after an oral glucose load (Rogers et al. 2005 Transplant Immunology 14: 67-75; Rogers et al. 2006 Transplant Immunology 16, 176-184). Cells expressing insulin and porcine proinsulin mRNA with beta cell morphology are reported to engraft in host mesentery, mesenteric lymph nodes, liver and pancreas post-transplantation (Rogers et al. 2005 Transplant Immunology 14: 67-75; Rogers et al. 2006 Transplant Immunology 16, 176-184; Rogers and Hammerman 2008 Organogenesis 4, 48-51). Cells originating from E28 pig pancreatic primordia are reported to engraft similarly in non immune-suppressed STZ-diabetic rhesus macaques (Rogers et al. 2007 Xenotransplantation 14, 591-602). Exogenous insulin requirements were shown to be reduced in transplanted macaques and porcine, but no primate insulin circulated following an intravenous glucose load. However, primates continued to require exogenous insulin to maintain euglycemia even after multiple transplantation surgeries (Rogers et al. 2007 Xenotransplantation 14, 591-602).

SUMMARY OF THE INVENTION

Provided herein is an approach to establish organogenetic tolerance via prior transplantation of pig embryonic pancreas, thereby enabling subsequent implantation of porcine islets in a subject without the need for immune-suppression.

One aspect provides a method for treating a pancreatic disorder in a subject in need thereof. One or more porcine pancreatic primordium, or a portion(s) thereof, is implanted into a mammalian subject. A period of time is allowed to pass sufficient to induce tolerance to porcine islet cells. Porcine islet cells are implanted into the mammalian subject. In some embodiments, the pancreatic disorder is diabetes mellitus. The porcine islet cells can produce, inter alia, insulin, thereby functioning to normalize glucose in the subject. In some embodiments, the requirement for immunosuppression is reduced or eliminated.

In some embodiments, the porcine pancreatic primordium is isolated about 7 days after formation of an embryonic pig pancreas. In some embodiments, the developmental age of the porcine pancreatic primordium is at least about E27 but not more than about E35. In some embodiments, the developmental age of the porcine pancreatic primordium is about E27, about E28, about E29, about E30, about E31, about E32, about E33, or about E34. In some embodiments, the developmental age of the porcine pancreatic primordium is about E28.

In some embodiments, the pancreatic primordium comprises at least one embryonic dorsal, ventral, or fused pancreatic primordium that is substantially non-vascularized at the time of the harvest. In some embodiments, the pancreatic primordium comprises at least one embryonic dorsal, ventral, or fused pancreatic primordium in which antigen presenting cells are absent or substantially reduced in number at the time of the harvest.

In some embodiments, at least about one pancreatic primordium, or an equivalent amount of portions of a pancreatic primordium, are implanted into the subject. In some embodiments, at least about 1 to about 20 pancreatic primordia, or an equivalent amount of portions of pancreatic primordia, are implanted into the subject. In some embodiments, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 pancreatic primordia, or an equivalent amount of portions of pancreatic primordia, are implanted into the subject.

In some embodiments, the pancreatic primordia are implanted at one or more positions selected from the group consisting of: peritoneal cavity; mesentery; near the subject's omentum adjacent to a branch of the subject's superior mesenteric artery; into a pouch of the omentum; in the subject's kidney capsule; under the subject's kidney capsule; within skeletal muscle; or in the subcutaneous space.

In some embodiments, the period of time sufficient to induce tolerance to porcine islet cells is at least about two weeks after implantation of the porcine pancreatic primordia. In some embodiments, the period of time sufficient to induce tolerance to a porcine islet cell is at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days, at least about 31 days, or at least about 32 days after implantation of the porcine pancreatic primordia. In some embodiments, the implanted porcine pancreatic primordia remain in place in the subject during the period of time sufficient to induce tolerance to porcine islet cells.

In some embodiments, the porcine islet cells are implanted into the subject in an amount of at least about 10,000 islet equivalents per kg of the subject. In some embodiments, the porcine islet cells are implanted into the subject in an amount of at least about 10,000; at least about 15,000; at least about 20,000; at least about 25,000; at least about 30,000; at least about 35,000; at least about 40,000; at least about 45,000; at least about 50,000; at least about 55,000; at least about 60,000; at least about 65,000; at least about 70,000; at least about 75,000; at least about 80,000; at least about 85,000; at least about 90,000; at least about 95,000; or at least about 100,000 islet equivalents per kg of the subject.

In some embodiments, the porcine islet cells are implanted at one or more sites selected from the group consisting of: intrahepatic islet infusion; intraportal injection; in the kidney capsule; underneath the kidney capsule; in the peritoneal cavity; in subcutaneous tissue; in the omentum; in epididymal fat; and in pancreas of the subject.

In some embodiments, the method also includes monitoring the subject for one or more of: implanted islet cell function; islet cell graft loss; insulin secretion, hematological and biochemical parameters; and plasma levels of porcine insulin.

In some embodiments, the mammalian subject is selected from the group consisting of: horse, cow, dog, cat, sheep, pig, mice, rat, monkey, guinea pig, chicken, and human. In some embodiments, the mammalian subject is a human.

In some embodiments, the diabetes mellitus comprises at least one of: Type 1 diabetes, Type 2 diabetes, pre-diabetes, gestational diabetes, congenital diabetes due to genetic defects of insulin secretion, cystic fibrosis-related diabetes, steroid diabetes induced by high doses of glucocorticoids, and monogenic diabetes. In some embodiments, the diabetes mellitus is Type 1 diabetes or Type 2 diabetes.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 7B, a subcapsular section from kidney; T, tubule, RC, renal capsule; FIG. 7C, a section of mesenteric lymph node, GC, germinal center, INSET enlargement; and FIG. 7D, renal cortex, T, tubule. Arrows (FIG. 7A-C) delineate pig X chromosomes. Scale bar: 10 µm (FIG. 7D).

FIG. 8A, Subcapsular space. T, renal tubule. Cell containing granules with a crystalline core surrounded by a clear space is delineated by an arrow; macrophages are delineated by arrowheads. FIG. 8B, Enlargement of macrophages. FIG. 8C, Enlargement of granules with a crystalline core surrounded by a clear space. Scale bar: 5 µm (FIG. 8A).

FIG. 14A shows the left kidney prior to retraction of the retroperitoneal membrane. FIG. 14B shows the left kidney after retraction of the retroperitoneal membrane. FIG. 14C shows the left kidney (left) and the right kidney (right) after removal from the rhesus macaque.

FIGS. 17A and 17C show pig X chromosomes in nuclei of cells from a normal porcine pancreas (arrow positive controls) stained using two different probes (green A; pink C). FIGS. 17B and 17D (arrows) show pig X chromosomes in the nuclei of cells in the mesenteric lymph node (FIG. 17B) and renal subcapsular space (FIG. 17D arrowheads). Scale bar: 10 um (FIG. 17A, FIG. 17B, FIG. 17C and FIG. 17D).

DETAILED DESCRIPTION OF THE INVENTION

Figure 1:
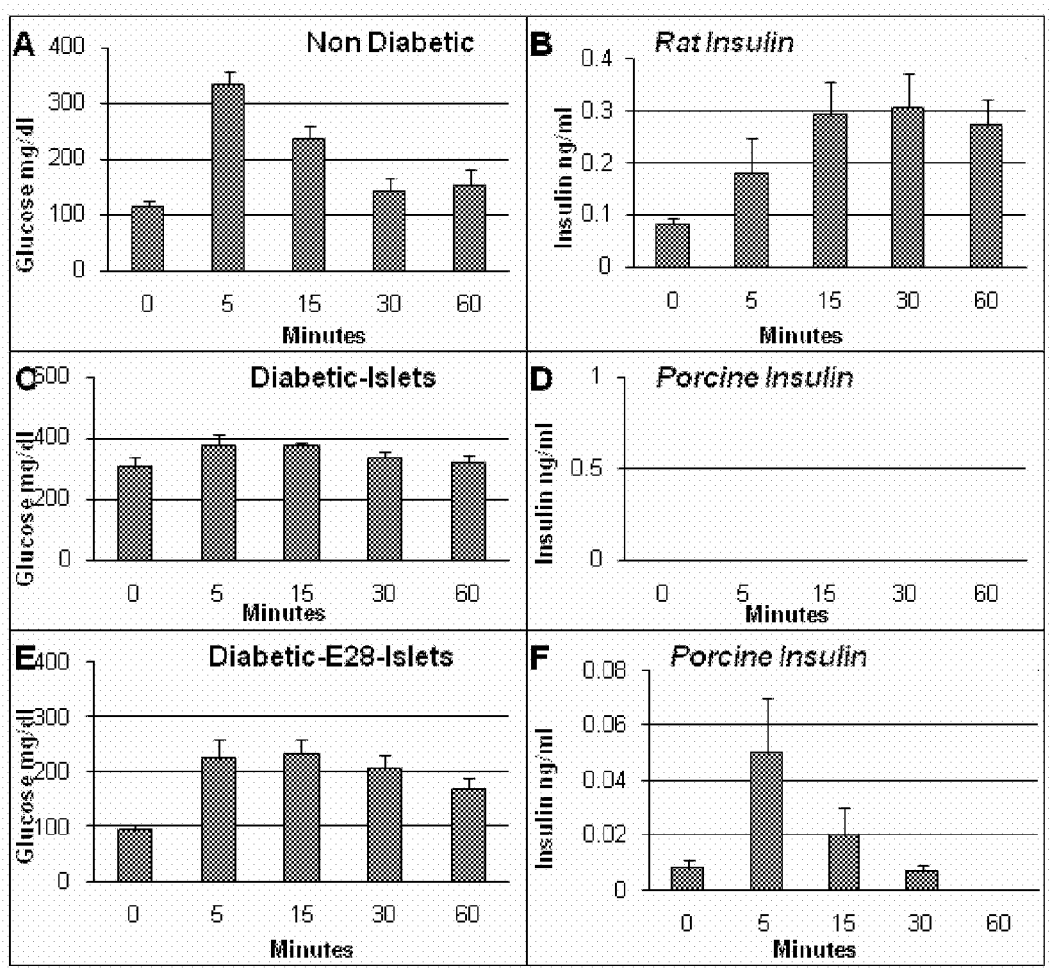
FIG. 1 is a series of bar graphs depicting levels of glucose and porcine insulin following administration of oral glucose to a STZ-diabetic rat. Levels of blood glucose (FIG. 1A, FIG. 1C, and FIG. 1E) and rat insulin (FIG. 1B) or porcine insulin (FIG. 1D and FIG. 1F) before (time 0) and following i.v. glucose administration to nondiabetic rats (FIG. 1A and FIG. 1B) or STZ-diabetic rats implanted with porcine islets (FIG. 1C and FIG. 1D) or STZ-diabetic rats transplanted with E28 pig pancreatic primordia and subsequently with porcine islets (FIG. 1E and FIG. 1F). Data are mean+/−SE of n=4 rats in each group.

The present application is based, at least in part, on the observation that pre-implantation of porcine pancreatic primordia cells in a mammalian subject can induce tolerance to subsequently implanted porcine mature islet cells without the need for immune-suppression. The ability to employ porcine islet transplants to normalize glucose tolerance in non-immune suppressed patients widens the applicability for and reduces the toxicity of transplantation therapy for diabetes mellitus.

Studies described herein show engraftment of cells originating from isolated porcine islets of Langerhans implanted beneath the renal capsule of non-immune-suppressed streptozotocin (STZ)-diabetic Lewis rats that previously had received pig pancreatic primordia transplants in mesentery, but not in kidneys of rats with no prior mesenteric pig pancreatic primordia transplants. Thus is demonstrated that cross tolerance to porcine pancreatic primordia cells can extend to the same or similar cell component present in porcine islets from adult swine (adult islets).

While intact porcine islets were not observed to engraft, a population of cells with beta cell morphology that express insulin and porcine proinsulin mRNA did engraft in kidneys of rats transplanted previously with pig pancreatic primordia. The presence of donor derived cells in kidneys was confirmed using fluorescent in-situ hybridization for the porcine X chromosome. Such observations are consistent with induction of tolerance to a cell component of adult porcine islets by previous transplantation of pig pancreatic primordia, a phenomenon designated herein as "organogenetic tolerance". Thus is established that prior transplantation of pig embryonic pancreas can enable the implantation of porcine islets in a mammalian subject without the need for immune-suppression.

While under no obligation to do so, and in no way limiting the invention, the following hypotheses for organogenetic tolerance is provided. Cells from pig pancreatic primordia may engraft in a non-immune-suppressed subject because the atypical pattern of the growth and differentiation of pig pancreatic primordia following implantation (i.e., no exocrine tissue; no islet formation) results in a pattern of antigen expression that is not recognized as foreign by the host. Another potential explanation is that migration of cells originating from primordia to mesenteric lymph occurs after mesenteric transplantation (resulting in mixed chimerism) that may render a host tolerant to a cellular component present in the primordia or that differentiates in situ following implantation.

Data presented herein establish that previous transplantation of pig embryonic pancreas can enable the implantation of porcine islets in a subject host without the need for immune-suppression. Organogenetic tolerance to pig islets can be established so as to normalize glucose tolerance in a subject thereby providing, for example, a transplantation therapy for human diabetics.

Pancreatic Primordia.

As described herein, implantation of porcine pancreatic primordia into a subject can establish organogenetic tolerance. Such tolerance can allow subsequent implantation of porcine islet cells with reduced or eliminated immunological reaction or complications.

Transplantation of embryonic pancreas to replace the function of diseased organs provides advantages relative to transplantation of either pluripotent embryonic stem cells, or of fully differentiated (adult) pancreas or islets. First, unlike embryonic stem cells, pancreatic primordia differentiate along defined organ-committed lines. For transplanted pancreatic primordia, there is no requirement to steer differentiation and a reduced or eliminated risk of teratoma formation. In the case of embryonic pancreas, the glucose sensing and insulin releasing functions of beta cells that differentiate from primordia are functionally linked. Second, the growth potential of cells within embryonic pancreas is enhanced relative to those in terminally-differentiated pancreas or islets. Third, the cellular immune response to transplanted primordia obtained early during embryogenesis is attenuated relative to that directed against adult pancreas or islets. Fourth, early organ primordia, including pancreatic primordia, are avascular. The ability of cellular primordia to attract a host vasculature renders them less susceptible to humoral rejection than is adult pancreas with donor blood vessels transplanted across a discordant xenogeneic barrier. Fifth, organ primordia differentiate selectively. In the case of embryonic pancreas, exocrine pancreatic tissue does not differentiate following transplantation, obviating complications that can result from exocrine components such as the enzymatic autodigestion of host tissues.

While glucose tolerance can be normalized in a non-immune-suppressed formerly diabetic subject by transplantation of pig pancreatic primordia, weight of the subject can be a factor. For example, while glucose tolerance can be normalized in non-immune-suppressed formerly diabetic rats by transplantation of E28 pig pancreatic primordia (Rogers et al. 2004 Am. J. Physiol. 286, E502-E509; Rogers et al. 2005 Transplant Immunology 14: 67-75; Rogers et al. 2006 Transplant Immunology 16, 176-184; Rogers and Hammerman 2008 Organogenesis 4, 48-51), it has proven to be more difficult to normalize glucose tolerance in non immune-suppressed rhesus macaques (Rogers et al. 2007 Xenotransplantation 14, 591-602). One explanation is that a macaque weighs approximately 20 times as much as a rat. A STZ-diabetic rat can be rendered normoglycemic by transplantation of 5 pig pancreatic primordia (Rogers et al. 2006 Transplant Immunology 16, 176-184; Rogers and Hammerman 2008 Organogenesis 4, 48-51). Extrapolating, it may take about 100 primordia to normalize glucose tolerance in a subject the size of a rhesus macaque. This would require the sacrifice of about 7 pregnant sows and would require a good deal of surgical time with the attendant complications. Further extrapolation suggests that it may take about 1,000 primordia to normalize glucose tolerance in a human subject. The approach described herein avoids relying solely upon transplanted primordia to normalize glucose tolerance.

In lieu of increasing the number of transplanted primordia to normalize glucose tolerance in a subject, the approach described herein substitutes implanted porcine islets, a more easily obtainable and possibly more concentrated source of insulin-producing cells, in a subject rendered tolerant to pig pancreatic primordia. As demonstrated herein, previous transplantation of the primordia renders a host subject tolerant to islets (see Examples 5-6).

The pancreatic primordia can comprise at least one embryonic dorsal or ventral pancreatic anlage that is substantially non-vascularized within the donor at the time of the harvest. Such tissue can further comprise both dorsal and ventral anlagen, one or more such anlagen, whole pancreata (both dorsal and ventral anlagen or fused anlagen), or such tissue from one or more donors.

A whole pancreatic primordium can be implanted. One or more portions of a pancreatic primordium can be implanted. Both a whole pancreatic primordium and one or more portions of a pancreatic primordium can be implanted. In one embodiment, the one or more portions of a primordium for implantation are non-digested, non-disassociated portions of such tissue. In another embodiment, the one or more portions of a pancreatic primordium for implantation are digested or disassociated portions of such tissue, and optionally cultured.

Pancreatic primordia can be harvested from at least one donor at a suitable stage of development. For example, a pancreatic primordium tissue can be harvested immediately before or within days after the dorsal and ventral anlagen become fused or prior to vascularization or prior to the creation and distribution within the tissue of antigen-presenting cells by the donor. Pancreatic primordia can be harvested soon after the immature pancreas begins formation and can be dissected free from the donor tissues prior to the presence of blood vessels that either originate within the pancreas or from outside the pancreas. Pancreatic primordia can be harvested prior to vascularization and before mature antigen presenting cells have formed in the developing embryos from which the pancreatic primordia are obtained, or prior to the time when, mature antigen presenting cells have not migrated into the avascular pancreatic anlage. At such stage of development, the immature pancreatic tissue can be considered free or at least substantially free of antigen-presenting cells.

Tissue harvested too late in the development of the pancreas, for example, tissue having visible blood vessels, may contain more antigen-presenting cells and cell-surface antigens and thus present more of a threat of rejection by the recipient. Tissue harvested at timing of developmental and vascularization recited herein can be substantially free of antigen presenting cells, which may reduce the chance of acute rejection. Tissue harvested at timing of developmental and vascularization recited herein can be substantially free of antigens that are causative of humoral rejection (hyperacute or acute vascular rejection). Furthermore, pancreatic primordia harvested during the developmental stage described herein are of relatively small size, which decreases the time during which harvested and implanted tissue does not have access to nutrients relative to implanted tissues.

The specific developmental stage for harvesting the pancreatic tissue will vary depending upon the species of donor. In pigs, the pancreas forms at the end of the first month of a 115 day gestation period. A pancreatic primordium for implantation into a subject according to methods described herein can be harvested from a pig within about 7 days after formation of the embryonic pancreas. A pancreatic primordium for implantation into a subject according to methods described herein can be harvested from a pig prior to E35. For example, a pancreatic primordium can be harvested from a pig of about E28 and implanted into a subject. A pancreatic primordium for implantation into a subject according to methods described herein can be harvested from a pig of at least E27 but prior to E35. For example, a pancreatic primordium can be harvested from a pig of about E27, about E28, about E29, about E30, about E31, about E32, about E33, or about E34. As another example, a pancreatic primordium can be harvested from a pig at E27, E28, E29, E30, E31, E32, E33, or E34. Preferably, a pancreatic primordium for implantation into a subject according to methods described herein is harvested from a pig at E28.

The amount of pancreatic primordia implanted into a subject is generally an amount sufficient to induce tolerance to subsequently implanted porcine mature islet cells. At least about one pancreatic primordium, or an equivalent amount of portions of pancreatic primordia, can be implanted into a subject. For example, at least about 2 to about 3 pancreatic primordia, or an equivalent amount of portions of pancreatic primordia, can be implanted into a subject. While there is no upper limit of pancreatic primordia, or equivalent portions thereof, that can be implanted, increased amounts of transplanted material requires additional donor material, additional implantation surgery, and complications inherent thereto. In some embodiments, up to about 20 pancreatic primordia, or an equivalent amount of portions of pancreatic primordia, can be implanted into a subject. For example, at least about one pancreatic primordium up to about 20 pancreatic primordia, or an equivalent amount of portions of pancreatic primordia, can be implanted into a subject. As another example, at least about 5 pancreatic primordia up to about 10 pancreatic primordia, or an equivalent amount of portions of pancreatic primordia, can be implanted into a subject. As a further example, at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 pancreatic primordia, or an equivalent amount of portions of pancreatic primordia, can be implanted into a subject.

Pancreatic primordia can be implanted in a variety of locations in the subject, as known in the art (see e.g., U.S. Pat. No. 7,384,630, issued Jun. 10, 2008). For example, pancreatic primordia can be implanted into the peritoneal cavity. As another example, pancreatic primordia can be implanted in the mesentery. As another example, pancreatic primordia can be implanted near the omentum of a subject adjacent to a branch of the superior mesenteric artery. As another example, pancreatic primordia can be implanted into a pouch of the omentum. As another example, pancreatic primordia can be implanted under the kidney capsule. As another example pancreatic primordia can be implanted within skeletal muscle (see e.g., Adams et al. 1997 J Surgical Res 68, 73-78) or in the subcutaneous space (see e.g., Gunawardana et al. 2008 Am J Physiol Endocrinol Metab 296, E323-E332), which could be done under local anaesthesia. Implantation of pancreatic primordia into a subject can be according to methods known to one of ordinary skill in the art.

A pancreatic primordium implanted using the techniques described herein is usually initially non-vascularized and, therefore, can grow and become vascularized at least in part by the subject's blood vessels. While an implanted pancreatic primordium is intended to induce tolerance to subsequently implanted porcine islet cells and is not intended to normalize glucose itself, a pancreatic primordium may itself form a chimeric pancreata characterized by the formation of mature and functioning islets or endocrine cells, producing at least insulin and possibly, glucagon and somatostatin.

A pancreatic primordium can be adapted for implantation by preparing it for or maintaining it in the cold (approximately 4 degrees Celsius) after harvesting but prior to implantation. A pancreatic primordium can be contacted with growth factors, growth medium, or other compounds and compositions to enhance the post-implantation growth and development of the tissue. For example, pancreatic primordia can be contacted with a composition comprising hepatocyte growth factor (preferably 10-9 M) and VEGF (preferably 5 ug/ml) in HamsF12:Dulbecco's modified Eagles medium (preferably 50 to 100 ul of a 50:50 mix) post-harvest and prior to implantation, preferably for about 45 minutes to about 3 hours at about 4 degrees Centigrade.

Time Between Pancreatic Primordia and Islet Cell Implantation.

Described herein is an approach in which prior implantation of porcine pancreatic primordia establishes organogenetic tolerance to subsequently implanted porcine islet cells. The period of time between implantation of porcine pancreatic primordia and implantation porcine islet cells is generally at least that amount of time sufficient for tolerance to be induced. Implantation of porcine islet cells can occur at least about two weeks after implantation of porcine pancreatic primordia.

For example, implantation of porcine islet cells can occur at least about three weeks after implantation of porcine pancreatic primordia. As another example, implantation of porcine islet cells can occur at least about four weeks after implantation of porcine pancreatic primordia. As another example, implantation of porcine islet cells can occur at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days, at least about 31 days, or at least about 32 days, or more, after implantation of porcine pancreatic primordia.

Usually, implantation of porcine islet cells can occur at any time after tolerance has been induced and the implanted porcine pancreatic primordia remain in the subject. As such, there is not necessarily a fixed upper time limit for implantation of porcine islet cells after implantation of porcine pancreatic primordia. Preferably, porcine islet cells are implanted after organogenetic tolerance is induced and while implanted porcine pancreatic primordia remain in place in the subject.

Tolerance as used herein is understood to be immune unresponsiveness in the absence of ongoing therapy to graft antigens, but not to other (third-party) antigens. Functional characteristics of tolerance include one or more of the following: lack of demonstrable immune reactivity to graft antigens; presence of immune reactivity to other antigens; and absence of generalized immunosuppression for graft maintenance. A tolerant subject can retain a functional graft, retain immune reactivity to other foreign antigens, and avoid the risk of generalized immunosuppression.

Porcine Islet Cells.

As described herein, porcine islet cells can be implanted into a subject with organogenetic tolerance induced by prior implantation of porcine pancreatic primordia. Such an approach provides for transplantation of porcine islet cells into a mammalian subject with reduced or eliminated immunological reaction or complications.

Porcine islet cells can be harvested according to methods known in the art (see e.g., Example 6; Swanson et al. 2001 Human Immunology 62, 7390-749; Casu et al. 2008 Diabetologia 51, 120-129; Cantarovich et al. 2002 Xenotransplantation 9, 25-35; Groth et al. 1999 J Mol Med 77, 153-154). Porcine islet cells can include one of more of α cells, which secrete glucagon; β cells, which secrete insulin; δ cells, which secrete somatostatin; PP cells, which secrete pancreatic polypeptide, and stem cells capable of undergoing differentiation into mature and functional islet components. Preferably, the porcine islet cells substantially comprise porcine β islet cells; more preferably, the porcine islet cells substantially comprise porcine β islet cells and stem cells.

Porcine islet cells can be harvested from, for example, adult pig pancreas or fetal pig pancreas. Porcine islet cells, as that term is used herein, include islet-like cell clusters (ICC) obtained from digested and cultured fetal pig pancreas tissue (see e.g., Groth et al. 1999 J Mol Med 77, 153-154). Porcine islet cells can be assessed for islet function in vivo or in vitro according to methods known in the art. For example, porcine islet cells can be assessed for islet function by a static incubation test (see e.g., Cantarovich et al. 2002 Xenotransplantation 9, 25-35).

Porcine islet cells can be implanted according to processes known in the art (see e.g. Example 6; Hering and Walawalkar 2009 Transplant Immunology 21, 81-86; Groth et al. 1999 J Mol Med 77, 153-154; Cantarovich et al. 2002 Xenotransplantation 9, 25-35; Cardona et al. 2006 Nature Medicine 12(3), 304-306; Hering et al. 2006 Nature Medicine 12(3) 301-303; Casu et al. 2008 Diabetologia 51, 120-129). Except as otherwise noted herein, therefore, implantation of porcine islet cells into mammalian subject can be carried out in accordance with such processes. Notably, the process described herein provides for implantation of porcine islets in a mammalian subject without the need for immune-suppression, in contrast to conventional protocols.

The amount of porcine islet cells implanted into a subject can be determined according to a desired therapeutic outcome. The amount of porcine islet cells selected for implanting in a subject according to methods described herein can be an amount selected for a conventional immunosuppression-requiring islet cell implantation. In contrast to conventional techniques, in various embodiments described herein, such an amount of islet cells can be implanted but without any requirement for immunosuppression.

The amount of porcine islet cells implanted into a subject will vary depending upon the subject treated and the particular mode of administration. It will be appreciated by those skilled in the art that the unit content of porcine islet cells contained in at an implantation time or at an implantation site need not in itself constitute a therapeutically effective amount, as the necessary therapeutically effective amount could be reached by a plurality of implantations in the same or different sites.

The specific therapeutically effective level of porcine islet cells implanted into any particular subject can depend upon a variety of factors including the disorder being treated and the severity of the disorder; activity of the specific cells employed; the specific type of cells employed; the age, body weight, general health, sex and diet of the patient; the time of implantation; the route of implantation; the site of implantation; the rate of excretion or destruction of the implanted cells; the duration of the treatment; drugs used in combination or coincidental with the implanted porcine islet cells; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Shamel (2004) Applied Biopharmaceutics & Pharmacokinetics, McGraw-Hill/Appleton & Lange, ISBN 0071375503).

In some embodiments, an amount of porcine islet cells selected for implanting into a subject, or implanted into a subject, is an amount sufficient to normalize glucose tolerance in a subject.

In some embodiments, an amount of at least about 10,000 to at least about 100,000 islet equivalents per kg of the subject can be implanted. For example, an amount of at least about 10,000 islet equivalents per kg of the subject can be implanted. As another example, an amount of at least about 15,000 islet equivalents per kg of the subject can be implanted. As another example, an amount of at least about 20,000 islet equivalents per kg of the subject can be implanted. As another example, an amount of at least about 25,000 islet equivalents per kg of the subject can be implanted. As another example, an amount of at least about 30,000 islet equivalents per kg of the subject can be implanted. As another example, an amount of at least about 35,000 islet equivalents per kg of the subject can be implanted. As another example, an amount of at least about 40,000 islet equivalents per kg of the subject can be implanted. As another example, an amount of at least about 45,000 islet equivalents per kg of the subject can be implanted. As another example, an amount of at least about 50,000 islet equivalents per kg of the subject can be implanted. As another example, an amount of at least about 55,000 islet equivalents per kg of the subject can be implanted. As another example, an amount of at least about 60,000 islet equivalents per kg of the subject can be implanted. As another example, an amount of at least about 65,000 islet equivalents per kg of the subject can be implanted. As another example, an amount of at least about 70,000 islet equivalents per kg of the subject can be implanted. As another example, an amount of at least about 75,000 islet equivalents per kg of the subject can be implanted. As another example, an amount of at least about 80,000 islet equivalents per kg of the subject can be implanted. As another example, an amount of at least about 85,000 islet equivalents per kg of the subject can be implanted. As another example, an amount of at least about 90,000 islet equivalents per kg of the subject can be implanted. As another example, an amount of at least about 95,000 islet equivalents per kg of the subject can be implanted. As another example, an amount of at least about 100,000 islet equivalents per kg of the subject can be implanted.

For example, an amount of at least about 20,000 to at least about 100,000 islet equivalents per kg of the subject can be implanted. As another example, an amount of at least about 30,000 to at least about 100,000 islet equivalents per kg of the subject can be implanted. As another example, an amount of at least about 40,000 to at least about 100,000 islet equivalents per kg of the subject can be implanted. As another example, an amount of at least about 50,000 to at least about 100,000 islet equivalents per kg of the subject can be implanted. As another example, an amount of at least about 60,000 to at least about 100,000 islet equivalents per kg of the subject can be implanted. As another example, an amount of at least about 70,000 to at least about 100,000 islet equivalents per kg of the subject can be implanted. As another example, an amount of at least about 80,000 to at least about 100,000 islet equivalents per kg of the subject can be implanted. As another example, an amount of at least about 80,000 to at least about 100,000 islet equivalents per kg of the subject can be implanted. As another example, an amount of at least about 90,000 to at least about 100,000 islet equivalents per kg of the subject can be implanted.

Sites for implantation of porcine islet cells into a mammalian subject are known in the art (see e.g., Contreras 2008 15, 99-101). For example, porcine islet cells can be implanted via intrahepatic islet infusion. As another example, porcine islet cells can be implanted via intraportal injection. As another example, porcine islet cells can be implanted in the kidney capsule. As another example, porcine islet cells can be implanted underneath the kidney capsule. As another example, porcine islet cells can be implanted in the peritoneal cavity. As another example, porcine islet cells can be implanted in subcutaneous tissue. As another example, porcine islet cells can be implanted in the omentum. As another example, porcine islet cells can be implanted in epididymal fat. As another example, porcine islet cells can be implanted in the pancreas.

Porcine islet cells can be implanted into a subject at one or more locations. For example, porcine islet cells can be implanted into a subject in at least two locations. As another example, porcine islet cells can be implanted into a subject in at least three locations. As another example, porcine islet cells can be implanted into a subject in at least four, or more, locations.

Harvested tissue may be treated with various growth factors and growth promoting agents, or combinations thereof, to enhance implant development. For example, contacting harvested tissue with hepatocyte growth factor (HGF) may enhance beta cell proliferation and increases islet mass in vivo. Similarly, vascular endothelial growth factor (VEGF) may be used to increase vascularization of pancreatic islets. Other growth factors that may be employed to design and implement enhanced development and maturation protocols include, among others: the epidermal growth factor (EGF) family ligands, which can regulate the lineage determination of endocrine cells within pancreatic anlagen maintained in organ culture; betacellulin (BTC), which favors beta cell differentiation; and Neuregulin (NRG-4), which affects the development of somatostatin-producing delta cells; retinoid antagonists, which inhibit acinar differentiation in vitro; members of the transforming growth factor family (TGFs), growth factors (IGFs), gastrin, activin A, and members of the fibroblast growth factor (FGF) family.

Enhanced development of the implanted islet cells can be enhanced by post-surgical administration of insulin, particularly exogenous insulin, to the subject. In some embodiments, exogenous insulin is administered to a subject after implantation of porcine islet cells. Development of implanted islet cells can be enhanced by post-surgical administration of other agents known to stimulate beta cell development, such as glucagon-like peptides (Williams 2009 Endocrinology 150, 2997-3001).

Implanted islet cell function can be assessed according to methods known in the art. For example, implanted islet cell function can be assessed according to an oral or intravenous glucose tolerance test (e.g., a monthly oral or intravenous glucose tolerance test). As another example, the subject can be assessed by periodic blood sampling to evaluate parameters such as insulin secretion, and standard hematological and biochemical parameters. Islet cell graft loss can be assessed according to methods known in the art. For example, graft loss can be assessed by periodic monitoring of porcine insulin using mass spectrometry (Rogers et al. 2007 Xenotransplantation 14, 591-602), where graft loss can be defined as two or more consecutive negative plasma levels of porcine insulin.

Subject.

Described herein is an approach to establish organogenetic tolerance in a mammalian subject via prior transplantation of pig embryonic pancreas, thereby enabling subsequent implantation of porcine islets without the need for immune-suppression.

Methods described herein are generally performed on a subject in need thereof. A determination of the need for treatment will typically be assessed by a history and physical exam consistent with a disease or disorder associated with pancreatic function. Diagnosis of the various conditions treatable by the methods described herein is within the skill of the art. A disease or disorder associated with pancreatic function includes, but is not limited to diabetes, e.g., Type II or Type I diabetes. A subject in need of methods described herein can exhibit reduced functional pancreatic mass as a result of suffering from a pancreatic-associated disease or disorder.

A subject in need of methods described herein can have, be diagnosed as having, or be at risk for, diabetes mellitus. Specific forms of diabetes mellitus treatable according to methods described herein include, but are not limited to, Type 1 diabetes, Type 2 diabetes, pre-diabetes, gestational diabetes, congenital diabetes due to genetic defects of insulin secretion, cystic fibrosis-related diabetes, steroid diabetes induced by high doses of glucocorticoids, or monogenic diabetes. Diagnosis of diabetes mellitus treatable by the methods described herein is within the skill of the art. Symptoms of diabetes mellitus may include are polyuria, polydipsia, rapid yet significant weight loss, irreducible mental fatigue, blurred or changed vision, Kussmaul breathing, nausea, vomiting, and abdominal pain. Diagnosis of diabetes mellitus can be made, for example, by demonstrating one or more of: fasting plasma glucose level at or above 126 mg/dL (7.0 mmol/l); plasma glucose at or above 200 mg/dL (11.1 mmol/l) two hours after a 75 g oral glucose load as in a glucose tolerance test; and symptoms of hyperglycemia and casual plasma glucose at or above 200 mg/dL (11.1 mmol/l). According to generally accepted standards, two fasting glucose measurements above 126 mg/dL (7.0 mmol/l) can be considered diagnostic for diabetes mellitus.

Treatment in accord with the methods described herein can be performed prior to, concurrent with, or after conventional treatment modalities for pancreatic disorders, such as diabetes mellitus.

The subject receiving the porcine pancreatic primordia and islet cells can be a mammalian subject. The subject can be, for example, a horse, cow, dog, cat, sheep, pig, mice, rat, monkey, guinea pig, and chicken, or human. Preferably, the subject is a human. More preferably, the subject is a human having, or diagnosed with having, Type II or Type I diabetes.

Formulation.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, preferably in purified form, together with a suitable amount of carrier so as to provide the form for proper administration to the subject.

The formulation should suit the mode of administration. The agents of use with the current invention can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Methods, cells, and agents described herein can also be used in combination with other therapeutic modalities. Thus, in addition to the therapies described herein, one may also provide to the subject other therapies known to be efficacious for treatment of the disease, disorder, or condition.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

Definitions and methods described herein are provided to better define the present invention and to guide those of ordinary skill in the art in the practice of the present invention. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Induction of Diabetes Mellitus and Treatment with Exogenous Insulin

Diabetes mellitus was induced in female LEW rats by a single i.p. injection of 40-50 mg/kg STZ. Rats were considered diabetic if fasting blood glucose levels were 300 mg/dl or above 5 consecutive days after STZ administration, at which time E28 pig pancreatic primordia were implanted. Maintenance of glucose levels <250 mg/dl during the first 2-3 weeks post-transplantation is necessary to permit optimal differentiation, proliferation, and function of transplanted E28 pig pancreatic primordia (Rogers and Hammerman 2008 Organogenesis 4, 48-51). Accordingly, rats transplanted with pig pancreatic primordia or islets were treated with 1-2 units sq b.i.d. of Lantus insulin (Sanofi-Aventis, Bridgewater, N.J.) for 2-3 weeks after implantation to maintain fasting glucose levels, measured every 3 days, at 200-250 mg/dl (Rogers and Hammerman 2008 Organogenesis 4, 48-51).

Example 2

Glucose and Insulin Measurements

Levels of glucose were measured using the Hemocue B-glucose Analyzer (Hemocue, Lake Forest, Calif.) in whole blood obtained (via tail vein) at 8 AM after an overnight fast. Insulin in serum was measured using one of two enzyme-linked immunosorbent assays (ELISAs): 1) A porcine insulin-specific ELISA (catalog number K6219; DakoCytomation, Carpinteria Calif.; sensitivity 0.02 ng/ml) that does not detect rat insulin was used to generate data shown in FIGS. 1, D and F. Insulin measured using this ELISA is designated porcine insulin; or 2) an ultrasensitive ELISA (Mercodia, Winston-Salem, N.C.; NVC 10-1137-01, sensitivity 0.01 ng/ml) that detects rat insulin, but cross-reacts with porcine insulin was used to generate data from rats into which no pig tissue is present shown in FIG. 1B. Insulin measured using this ELISA is designated rat insulin. Levels of C-peptide were measured using an ELISA specific for rat (number 10-1172-01; Mercodia). Intravenous glucose tolerance testing (Rogers et al. 2003 ASAIO 49, 527-532) was performed by infusing D-glucose (0.1 g/kg body weight) via rapid injection into one tail vein and collecting blood samples from the other. Multiple Comparisons were performed using the Bonferroni multiple comparisons test (GraphPad Instat 3; GraphPad, San Diego Calif.). Differences were considered significant if $P<0.05$ by two-tailed analysis.

Example 3

Histology

Tissues removed from hosts were fixed in 10% phosphate-buffered formalin (see Rogers et al. 2004 Am. J. Physiol. 286, E502-E509; Rogers et al. 2005 Transplant Immunology 14: 67-75; Rogers et al. 2006 Transplant Immunology 16, 176-184; Rogers and Hammerman 2008 Organogenesis 4, 48-51; Rogers et al. 2007 Xenotransplantation 14, 591-602). The fixative was removed, and tissues embedded in paraffin, sliced into 5 um sections and placed on glass slides in preparation for staining. Polyclonal rabbit anti-insulin serum (Accurate Chemicals, Westbury, N.Y.) was used to detect insulin in tissue sections. Nonimmune rabbit serum was substituted for control stains. 8 Sections were counterstained using hematoxylin.

Example 4

Detection of Insulin Transcripts Using In-Situ Hybridization, Fluorescent In Situ Hybridization, and Electron Microscopy In situ hybridization was performed on sliced 5 um paraffin-embedded sliced tissue sections using a kit from GeneDetection (Bradenton Fla.) (see Rogers et al. 2007 Xenotransplantation 14, 591-602). Digoxin-labeled antisense probes (GeneDetection), that detect porcine, but not rat transcripts were complementary to nucleotides 230-264 of porcine preproinsulin cDNA: 5'-GGCGGAGAACCCTCAGGCAGGT-GCCGTGGAGCTGG-3' (SEQ ID NO: 1) (Genbank: AY044828). A sense probe was used for control stains.

Fluorescence in situ hybridization in paraffin-embedded tissue sections was performed as per instructions provided by Cambio (Cambridge, U.K.). Three- to 6-μm tissue sections were dewaxed in xylene; rehydrated through graded alcohols (95; 80; 60; and 35%) to water; incubated with sodium thiocyanate solution (16 g dissolved in 200 ml of water) for 10 minutes at 80° C.; washed in phosphate-buffered saline (PBS) for 10 minutes at 37° C.; incubated in a pepsin solution (0.8 g of pepsin in 200 ml of 0.1 M HCl) for 10 minutes at 37° C.; quenched in a glycine solution [0.4 g of glycine in 200 ml of double concentration PBS (2 mg/ml)]; washed in PBS; post-fixed in a paraformaldehyde solution (8 g of paraformaldehyde in 200 ml of PBS at 80° C., cooled to room temperature before use) for 2 minutes; washed in PBS X3; dehydrated through graded alcohols; and air-dried. Prediluted Cambio X-paint mix (CA-1865-XF) was removed from the freezer and warmed to 37° C. before 10-15 μl being applied to the center of the slide that was subsequently covered with a glass coverslip and sealed with rubber cement. The sealed slide was denatured at 80° C. for 10 minutes and hybridized overnight in a humid chamber. The next day, coverslips were removed and the slide was washed in a formamide wash solution [50 ml deionized formamide mixed with 50 ml of 2× standard saline citrate (SSC)] 37° C. for 3 changes of 5 minutes each; washed with a stringency wash solution (2× standard saline citrate) at 37° C. for 3 changes over 15 minutes; washed with a detergent wash solution (0.1 ml of 10% Tween 20 to 200 ml of 4 standard saline citrate) at 37° C. for 10 minutes; washed with PBS three times; mounted in 4',6'-Diamidino-2-Phenylindole Mountant (catalog number 1124-MT-50/1250) and visualized using an Olympus BX61 epifluorescence microscope with software that enables generation of composite images using multichannel monochrome captures.

Transmission electron microscopy was performed (see Rogers et al. 2005 Transplant Immunol 14, 67-75) using paraffin embedded tissue subsequently deparaffinized in xylene and postfixed in osmium.

Example 5

Isolation and Transplantation of Pancreatic Primordia

Unless otherwise indicated, methods are according to Examples 1-4.

At 28 days gestation, pregnant Yorkshire pigs (Oak Hill Genetics, Ewing, Ill.) were intubated and anesthesia maintained by inhalation of isoflurane and $O_2$ to effect. The uterus was removed, and the donor pig was then euthanized. Pancreatic primordia from E28 pig embryos were surgically isolated under a dissecting microscope. After isolation, primordia were placed immediately into ice-cold Dulbecco's modified Eagle's Medium:Ham's F12 containing iron-saturated transferrin (5 μg/ml), 25 nmol/L prostaglandin E1 and, 5 μg/ml recombinant human vascular endothelial growth factor (Genentech) and $10^{-8}$ M recombinant human hepatocyte growth factor (HGF) (Upstate Biotechnology, Lake Placid, N.Y.). After 45 minutes, six to eight pancreatic primordia were implanted between layers of mesentery of 6- to 10-week-old STZ-diabetic female LEW rat hosts in close proximity to blood vessels. Rats subjected to sham surgery had mesentery prepared for transplantation, but no E28 primordia were transplanted. Host rats received no immune suppression.

Example 6

Isolation and Transplantation of Porcine Islets of Langerhans

Unless otherwise indicated, methods are according to Examples 1-5.

Porcine islets of Langerhans were isolated from female Yorkshire pigs as described in Swanson et al. 2001 Human Immunology 62, 739-749. Five thousand islets equivalents (islets), suspended in medium 199 (Sigma-Aldrich, St. Louis, Mo.) were implanted beneath the renal capsule of STZ-diabetic rats using the technique described for transplantation beneath the renal capsule of kidney primordia (Rogers et al. 1998 Kidney Int 54, 27-37). Unless otherwise noted, rats had been transplanted in mesentery with E28 pig pancreatic primordia 8 weeks previously. In preliminary experiments using STZ-diabetic LEW rats, the fasting blood glucose levels and glucose tolerance of which had been normalized within 4 weeks of transplantation of E28 pig pancreatic primordia (Rogers et al. 2004 Am J Physiol 286, E502-E509; Rogers et al. 2005 Transplant Immunol 14, 67-75) subsequent implantation of islets in kidney resulted in severe hypoglycemia and death. Accordingly, for islet implantation studies reported here, we used rats, glucose levels in which were reduced by transplantation of E28 pig pancreatic primordia but not to levels in nondiabetic animals. Approximately one in three transplanted rats will manifest such a partial response (Rogers et al. 2009 Xenotransplantation 14, 591-602). Glucose tolerance can be normalized in such animals by retransplantation of E28 pig pancreatic primordia (Rogers et al. 2009 Xenotransplantation 14, 591-602). However, levels of fasting blood glucose do not normalize over time if no further transplantation is performed.

Example 7

Induction of Tolerance to a Cellular Component of Adult Porcine Islets by Previous Transplantation of E28 Pig Pancreatic Primordia This example demonstrates induction of tolerance to a cellular component of adult porcine islets by previous transplantation of E28 pig pancreatic primordia.

Unless otherwise indicated, methods are according to Examples 1-6.

Rats were rendered diabetic using STZ. Five days later a group into which porcine islets would be implanted 8 weeks later without prior transplantation of E28 pig pancreatic primordia (Diab-Islets) underwent sham surgery (n=4). Another group was transplanted with E28 pig pancreatic primordia (n=10) and subdivided into three subgroups. Eight weeks after transplantation of E28 pig pancreatic primordia: rats in one subgroup (Diab-E28-E28) were transplanted with E28 pig pancreatic primordia a second time (n=3); rats in a second subgroup (Diab-E28) received no further transplants (n=3); rats in a third subgroup (Diab-E28-Islets) were implanted with porcine islets (n=4). At 5 days after STZ administration and before any transplantation (before transplantation), fasting glucose levels in rats that were to be divided into each group averaged >300 mg/dl and were not different, one from the other (see e.g., Table 1).

TABLE 1

Levels of Fasting Glucose (mg/dl) in Groups of Rats. Data are mean +/− SE.

| | Diab-E28-E28 | Diab-E28 | Diab-E28-Islets | Diab-Islets |
|---|---|---|---|---|
| Before transplantation | | 384 +/− 26 (n = 6) | 359 +/− 11 (n = 4) | 378 +/− 5.0 (n = 4) |
| 8 weeks | | 232 +/− 7 (n = 6) | 213 +/− 34 (n = 4) | 309 +/− 38 (n = 4) |
| 12 weeks | 124 +/− 1 (n = 3) | 244 +/− 19 (n = 3) | 94 +/− 8 (n = 4) | 306 +/− 31 (n = 4) |

At 8 and 12 weeks post-transplantation of E28 pig pancreatic primordia in the Diab-E28 group, fasting glucose levels were significantly lower than before transplantation but did not differ from one another. In contrast, fasting glucose levels in the Diab-E28-E28 group measured at 12 weeks (124+/−1 mg/dl) were significantly lower than levels measured at 8 weeks in the Diab-E28 group and did not differ significantly from levels in a group of four nondiabetic rats (114+/−9 mg/dl). At 8 weeks post-transplantation of E28 pig pancreatic primordia in the Diab-E28-Islets group, fasting glucose levels were elevated relative to levels in the nondiabetic rats. However levels of glucose (94+/−8 mg/dl) measured at 12 weeks post-transplantation in the Diab-E28-Islets group (4 weeks after islet implantation) were not different from levels measured in the normal rats. Glucose levels at 8 in or 12 weeks from rats in the Diab-Islets group were not different from those measured before transplantation (see e.g., Table 1).

Thus, as reported previously (Rogers et al. 2009 Xenotransplantation 14, 591-602), re-transplantation of E28 pig pancreatic primordia normalizes glucose levels in rats not normalized by the first transplantation (Diab-E28-E28). However, implantation of islets also normalizes glucose levels in these rats (Diab-E28-Islets). In contrast, implantation of islets in sham-operated rats does not impact on levels of fasting glucose measured 4 weeks subsequently (Diab-Islets).

Shown in FIGS. 1, A, C, and E, are levels of glucose and shown in FIGS. 1, B, D, and F, are levels of venous insulin measured using the ELISA specific for porcine insulin (FIGS. 1, D and F) or the ELISA that detects both rat and pig insulin (FIG. 1B) each measured following administration of an i.v. glucose load to nondiabetic rats (FIGS. 1, A and B) or STZ-diabetic sham-operated rats 4 weeks after islet implantation (Diab-Islets) (FIGS. 1, C and D) or STZ-diabetic rats that had been transplanted with pig pancreatic primordia in mesentery and subsequently (4 weeks before i.v. glucose infusion) implanted with porcine islets in kidney (Diab-E28P-Islets) (FIGS. 1, E and F). Fasting glucose levels in nondiabetic rats (114+/−9 mg/dl) and rats in the Diab-E28-Islets group (94+/−8 mg/dl) were lower than those in the Diab-Islets group (306+/−32 mg/dl) but not different from one another at time 0. Levels in rats from the nondiabetic and Diab-E28-Islets groups increased following i.v. glucose infusion, but 60 minutes later were not different from levels measured at time 0. Glucose levels did not change significantly following glucose infusion in rats from the Diab-Islets group. No porcine insulin (<0.02 ng/ml) was detected detected at any time in rats from the Diabetic-Islets group (FIG. 1D). Rat insulin (measured using ELISA NVC 10-1137-01 in rats in which no pig tissue is present) (FIG. 1B) or porcine insulin (FIG. 1F), respectively, increased following the glucose infusion in nondiabetic rats and rats in the Diab-E28-Islets group. Levels of circulating porcine insulin in the Diab-E28-Islets group (FIG. 1F) were lower than corresponding levels of rat insulin in nondiabetic animals (FIG. 1B).

It is thought that recovery of native insulin secretion sufficient to normalize glucose tolerance has never been reported following administration of STZ to adult rats at comparable doses (see Rogers et al. 2004 J Physiol 286: E502-E509; Rogers et al. 2005 Transplant Immunol 14, 67-75; Rogers et al. 2006 Immunol 16, 176-184; Rogers et al. 2008 Organogenesis 4, 48-51), which is why such animals are appropriately used to evaluate the efficacy of transplantation procedures (see Hamamoto 2001 Biochem Biophys Res Commun 287, 104-109). But to provide additional evidence that the normalization of glucose tolerance shown in FIG. 1E did not result from recovery of endogenous insulin production of rats in the Diab-E28-Islets group, levels of rat C-peptide was measured and compared them to levels in nondiabetic rats or a group of four diabetic rats (diabetic). Levels of rat Cpeptide in diabetic rats or rats in the Diab-E28-Islets group did not differ one from the other, were comparable to levels measured by others in STZ-diabetic rats (see Cotter et al. 2003 Diabetes 52, 1812-1817) and were significantly lower than levels measured in Non Diabetic animals (see e.g., Table 2). These findings are consistent with the absence of recovery of native insulin production in rats from the Diab-E28-Islets group.

TABLE 2

Levels of Fasting Rat C Peptide (pmol/L) in Groups of Rats. Data are mean +/− SE of n = 4 rats in each group.

| Nondiabetic | Diabetic | Diab-E28-Islets |
| --- | --- | --- |
| 580 +/− 148 | 150 +/− 53 | 154 +/− 42 |

Figure 2:
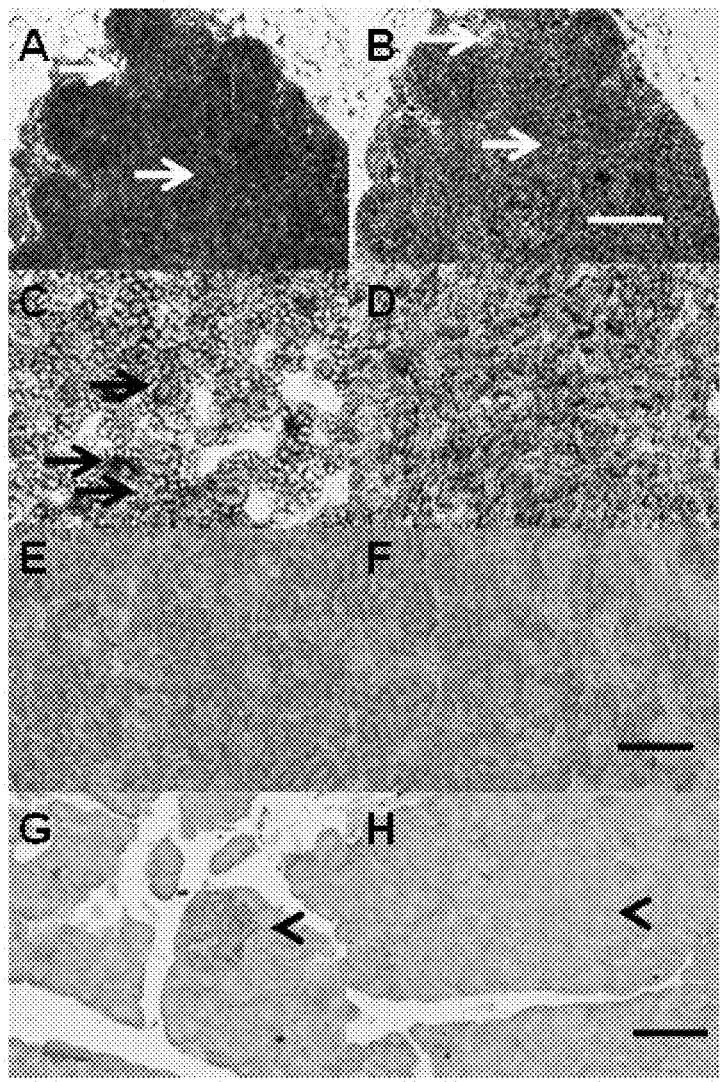
FIG. 2 is series of photomicrographs of mesenteric lymph node (FIGS. 2A-F) from a STZ diabetic rat into which E28 pig pancreatic primordia had been transplanted in the mesentery four weeks previously (FIGS. 2A-D) or a nontransplanted nondiabetic rat (FIG. 2E and FIG. 2F) or a pancreas from a nondiabetic nontransplanted rat (FIG. 2G and FIG. 2H) stained using anti-insulin antibody (FIG. 2A, FIG. 2C, FIG. 2E, and FIG. 2G) or control serum (FIG. 2B, FIG. 2D, FIG. 2F, and FIG. 2H). Arrows delineate tissue that stains positive for insulin (red-brown) (FIG. 2A and FIG. 2C) or negative staining tissue (FIG. 2B). Arrowheads delineate islet of Langerhans (FIG. 2G and FIG. 2H). Scale bars: 80 µm (A and B); 30 µm (FIG. 2-F); 100 µm (FIG. 2G and FIG. 2H).

Shown in FIG. 2, A-D, are tissue sections of mesenteric lymph nodes from a STZ-diabetic rat into which E28 pig pancreatic primordia had been transplanted in mesentery 4 weeks previously (Diab-E28) stained using antiinsulin antibody (FIGS. 2, A and C), or control antiserum (FIGS. 2, B and D). Sections 2A and 2B are consecutive. The arrows highlight areas of in FIG. 2A that contain insulin-positive cells relative to comparable areas in FIG. 2B. As before, in LEW rats (Rogers et al. 2004 J Physiol 286: E502-E509; Rogers et al. 2005 Transplant Immunol 14, 67-75; Rogers et al. 2008 Organogenesis 4, 48-51) or rhesus macaques (Rogers et al. 2009 Xenotransplantation 14, 591-602) transplanted with pig pancreatic primordia in mesentery, the insulin positive cells are located predominantly outside of germinal centers in medullary sinus (FIG. 2A, arrows). Individual insulin-positive cells cannot be delineated in FIG. 2A. However, individual insulin positive cells are evident in FIG. 2C that do not stain in sections stained using control antiserum (FIG. 2D). Shown in FIGS. 2, E and F, are sections of mesenteric lymph nodes and in FIGS. 2, G and H, are sections pancreas from a non-transplanted non-diabetic rat included as negative controls for lymph nodes from a transplanted rat and positive controls for insulin staining respectively. There is no insulin-positive tissue in lymph node tissue from the non-diabetic non-transplanted rat incubated with the anti-insulin antibody (FIG. 2E). As would be expected, the anti-insulin antibody stains β cells in an islet of Langerhans in the pancreas from the non-diabetic non-transplanted rat (arrowhead; FIG. 2G). Islet tissue does not stain if control antiserum is substituted (arrowhead; FIG. 2H).

Figure 3:
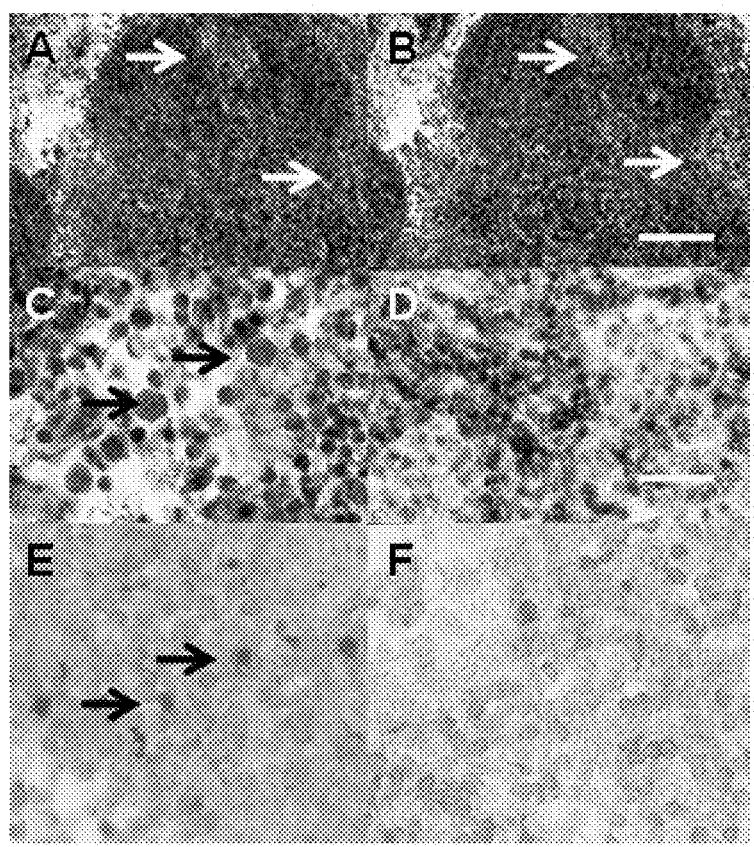
FIG. 3 is a series of photomicrographs of mesenteric lymph node from a formerly diabetic rat into which E28 pig pancreatic primordia and pig islets had been transplanted in the mesentery and kidney respectively stained using antiinsulin antibody (FIG. 3A and FIG. 3C) or control antibody (FIG. 3B and FIG. 3D) and sections hybridized to antisense (FIG. 3E) or sense (FIG. 3F) porcine proinsulin mRNA probes. Arrows delineate tissue that stains positive for insulin (red-brown) (FIG. 3A and FIG. 3C) or negative staining tissue (FIG. 3B) or positive staining for porcine proinsulin mRNA (FIG. 3E). Scale bars: 80 µm (FIG. 3A and FIG. 3B) and 25 µm (FIG. 3C-F).

FIG. 3 illustrates sections of mesenteric lymph node from a formerly diabetic rat following transplantation of embryonic pancreas in mesentery followed by implantation of pig islets in kidney (Diab-E28-Islets). FIGS. 3, A and B, is consecutive, and the arrows highlight comparable areas. Cells in medullary sinus expressing insulin stain with use of the anti-insulin antibody (FIGS. 3, A and C) but not the control antiserum (FIGS. 3, B and D). As for FIG. 2A, individual insulin-positive cells cannot be delineated in FIG. 3A. However, individual insulin positive cells are evident in FIG. 3C. Also shown in FIG. 3 are sections incubated with antisense (FIG. 3E) or sense (FIG. 3F) porcine proinsulin mRNA probes. As before (Rogers et al. 2006 Transplant Immunol 16, 176-184; Rogers et al. 2008 Organogenesis 4, 48-51), hybridization occurs in cells incubated with the antisense but not with the sense probe.

Figure 4:
FIG. 4 is a photograph of kidney from a STZ-treated rat transplanted previously with embryonic pig pancreas in mesentery. The photo was taken 4 weeks after implantation of pig islets in kidney. The whitish well-demarcated graft (white arrow) and the origin of a venous blood vessel (black arrow) are shown.

FIG. 4 is a photograph of a kidney from a STZ-treated rat that had been transplanted with embryonic pig pancreas in mesentery, taken 4 weeks after implantation of islets in kidney. As previously described by others in rat kidney following islet isotransplantation (Kallskog et al. 2006 Am J Transplant 6, 680-686), a distinct, whitish well-demarcated graft, which can be easily distinguished from the surrounding renal parenchyma is observed (white arrow) along with large intracapsular venous blood vessels that radiate from the graft out into the renal parenchyma (black arrow).

Figure 5:
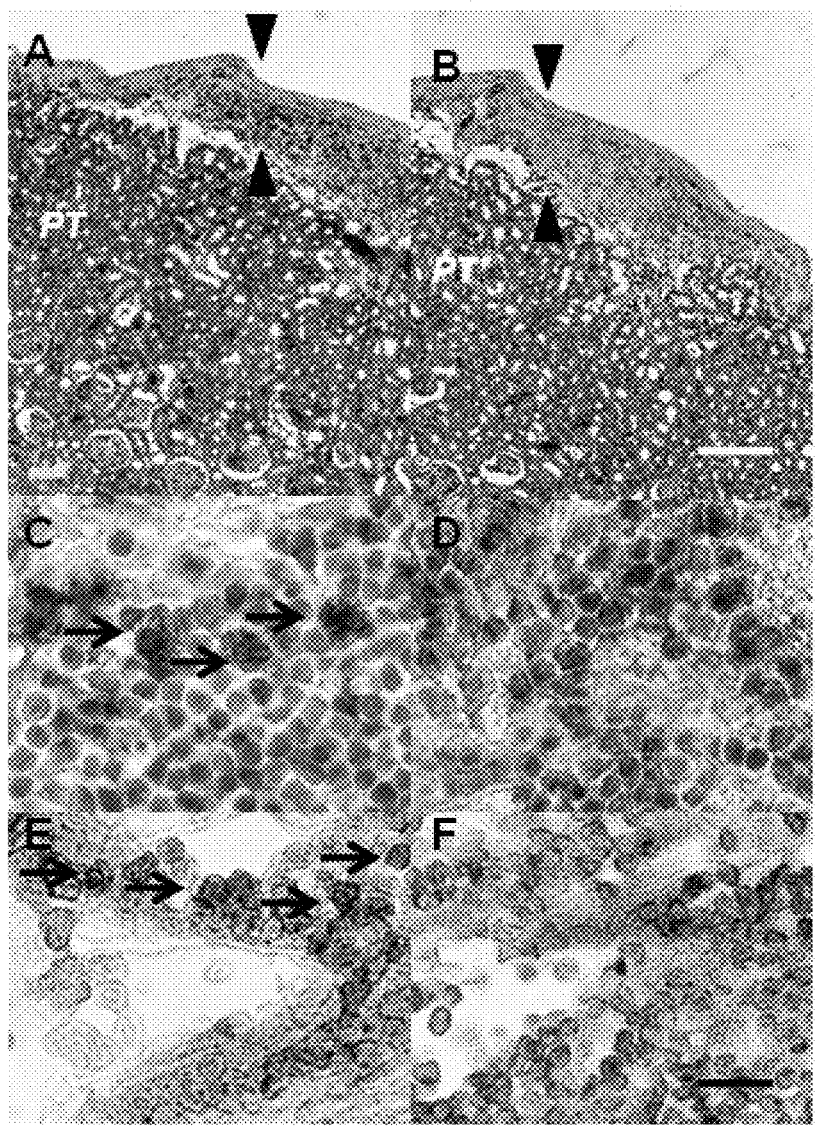
FIG. 5 is a series of photomicrographs of kidney from a diabetic rat into which embryonic pig pancreas had been transplanted in mesentery and pig islets had been transplanted subsequently in kidney stained using anti-insulin antibody (FIG. 5A and FIG. 5C) or control antibody (FIG. 5B and FIG. 5D) and sections hybridized to antisense (FIG. 5E) or sense (FIG. 5F) porcine proinsulin mRNA probes. Arrowheads delineate an expanded subcapsular space (FIG. 5A and FIG. 5B). Arrows delineate tissue in the subcapsular space that stains positive for insulin (red-brown) (FIG. 5C) or positive staining for porcine proinsulin mRNA (FIG. 5E). PT, FIG. 5A and FIG. 5B. Scale bars 80 µm (FIG. 5A and FIG. 5B) and 10 µm (FIG. 5C-F).

FIG. 5 shows sections from a kidney from a STZ-diabetic rat transplanted previously with embryonic pig pancreas in mesentery and subsequently with pig islets in kidney obtained 4 weeks after transplantation of islets. Sections are stained using anti-insulin antibodies (FIGS. 5, A and C) or control serum (FIGS. 5, B and D). As would be expected for kidney that filters, reabsorbs, and secretes insulin (Hammerman 1985 Am J Physiol 249:F1-F11) proximal tubules (PT) in FIG. 5A are positive (red brown) relative to comparable structures in FIG. 5B. Cells that stain for insulin (FIG. 5A), but not with control serum (FIG. 5B) are present in an expanded sub-capsular space (FIGS. 5, A and B, arrowheads). FIG. 5C shows a higher magnification of the subcapsular space. The cells that stain positive for insulin (red-brown stain) are polygonal with round nuclei and abundant cytoplasm (arrow), a β cell morphology (see Rogers et al. 2004 J Physiol 286: E502-E509; Rogers et al. 2005 Transplant Immunol 14, 67-75; Rogers et al. 2006 Immunol 16, 176-184; Rogers et al. 2008 Organogenesis 4, 48-51). Also shown in FIG. 5 are sections incubated with antisense (FIG. 5E) or sense (FIG. 5F) porcine proinsulin mRNA probes. Hybridization occurs with cells hybridized to the former (arrows) but not the latter probe.

Figure 6:
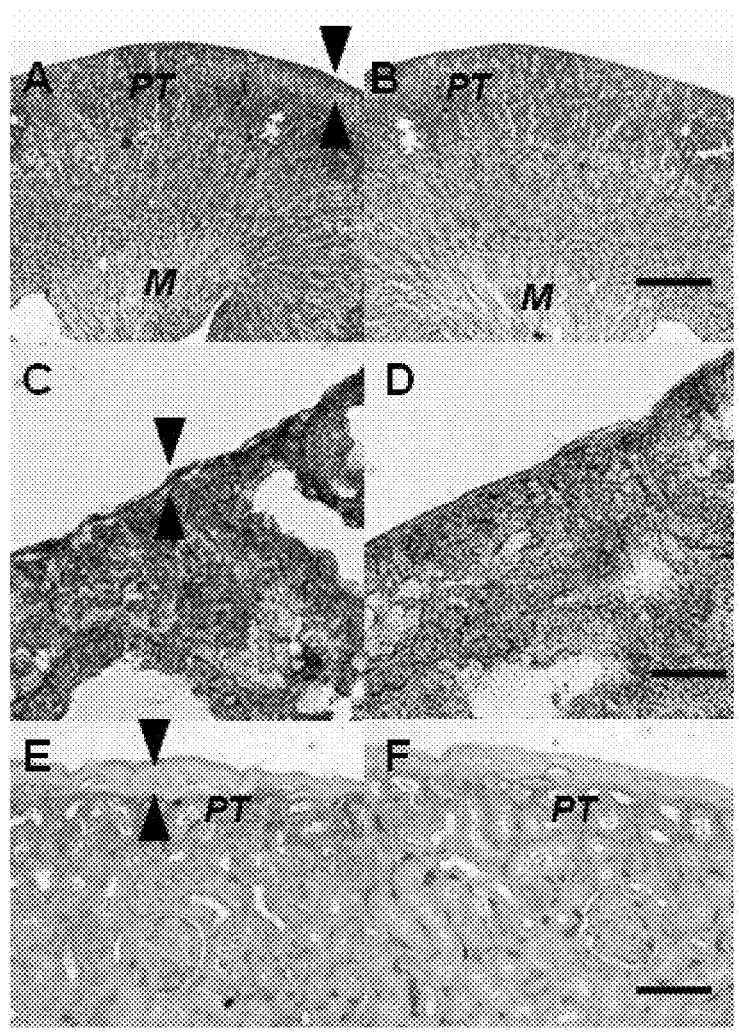
FIG. 6 is a series of photomicrographs of the contralateral kidney from a diabetic rat into which embryonic pig pancreas had been transplanted in the mesentery and pig islets had been implanted subsequently in the other kidney (FIG. 6A-D) or of a kidney from a diabetic rat in which pig islets had been implanted without prior transplantation of E28 pig pancreatic primordia (FIG. 6E and FIG. 6F) stained using anti-insulin antibody (FIG. 6A, FIG. 6C, and FIG. 6E) or control antiserum (FIG. 6B, FIG. 6D, and FIG. 6F). Arrowheads delineate a normal sized subcapsular space (FIG. 6A, FIG. 6C) or expanded subcapsular space (FIG. 6E). PT, proximal tubule FIG. 6A, FIG. 6B, FIG. 6E, and FIG. 6F. M, medulla (FIG. 6A and FIG. 6B). Scale bars: 100 µm (FIG. 6A and FIG. 6B), 10 µm (FIG. 6C and FIG. 6D), or 40 µm (FIG. 6E and FIG. 6F).

The contralateral (non-transplanted) kidney from a STZ-diabetic rat transplanted previously with embryonic pig pancreas in mesentery and subsequently with pig islets in the ipsilateral kidney is shown in FIG. 6, A-D. Sections obtained 4 weeks after islet transplantation are stained using anti-insulin antibodies (FIGS. 6, A and C) or control serum (FIGS. 6, B and D). A low magnification view of the contralateral kidney shows normal renal morphology with no evidence of engrafted tissue (FIGS. 6, A and B). As in FIG. 5, PT in FIG. 6A are positive (red brown) relative to comparable structures in FIG. 6B. Immunoreactive insulin (non-reabsorbed) (see Hammerman 1985 Am J Physiol 249:F1-F11) is also evident in the medulla (M) shown in FIG. 6A relative to FIG. 6B. In contrast to what is observed in the transplanted kidney (FIGS. 5, A and B), there is no expansion of the subcapsular space in the contralateral kidney (FIGS. 6, A and C, arrowheads) and no cells are present with β cell morphology as shown in FIG. 5, C. FIGS. 6, E and F, shows the subcapsular space of a kidney from a rat implanted with porcine islets 4 weeks previously with no prior transplantation of E28 pig pancreatic primordia (Diab-Islets). Sections are stained using anti-insulin antibodies (FIG. 6E) or control serum (FIG. 6F). Insulin staining of PT is evident in FIG. 6E. The subcapsular space (FIG. 6E, arrowheads) is expanded relative to that depicted in FIGS. 6, A and C. However, there are no cells with β cell morphology that stain for insulin (FIG. 6E).

These findings are consistent with induction of tolerance to a cellular component of adult porcine islets by previous transplantation of E28 pig pancreatic primordia, a phenomena designated as "organogenetic tolerance".

Example 8

Further Studies on Induction of Tolerance

Unless otherwise indicated, methods are according to Examples 1-7.

Figure 7:
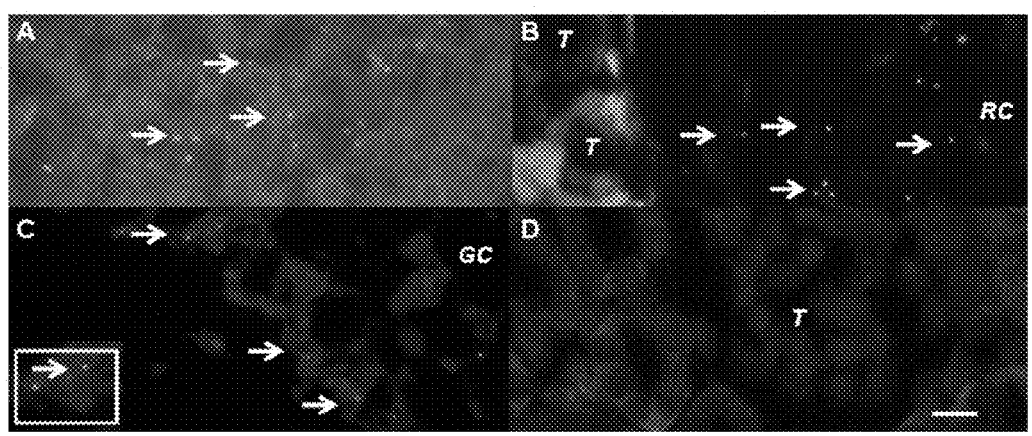
FIG. 7 is a series of fluorescence microscopy of tissue sections originating from a normal porcine pancreas (FIG. 7A) or a diabetic rat that had been transplanted with embryonic pig pancreas (FIG. 7B-D) in mesentery and subsequently with porcine islets in kidney.

To provide additional evidence that pig cells are present in kidneys and mesenteric lymph nodes of rats transplanted with pig pancreatic primordia and subsequently with porcine islets fluorescent in situ hybridization was performed using a probe specific for the pig X chromosome. Shown in FIG. 7A (arrows) are pig X chromosomes in nuclei of cells from a normal porcine pancreas (positive control). FIGS. 7, B and C (arrows), show, respectively, in tissue obtained 4 weeks after islet transplantation: pig X chromosomes in the nuclei of cells in the renal subcapsular space [between a tubule (T) and the renal capsule membrane (RC)]; and pig X chromosomes in the nuclei of cells outside of a germinal center (GC) of a mesenteric lymph node. There are no cells containing pig X chromosomes in renal cortex from the transplanted kidney (FIG. 7D), consistent with the subcapsular localization of the insulin positive and porcine proinsulin mRNA containing cells (FIG. 5) and with species specificity of the pig X chromosome probe (host rats are females).

Figure 8:
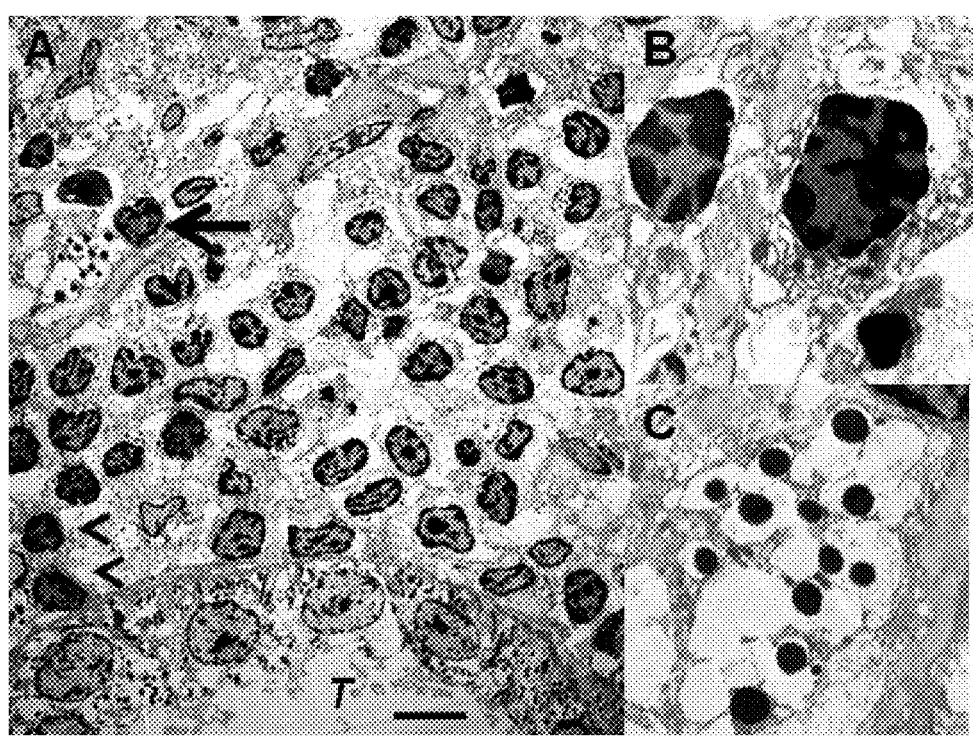
FIG. 8 is a series of Electron micrographs of rat kidney following sequential transplantation of E28 pig pancreatic primordia in mesentery and implantation of porcine islets in kidney.

It has been shown previously (Rogers et al. 2005 Transplant Immunol 14, 67-75) using electron microscopy that cells with β cell morphology containing granules, some of which have a crystalline core surrounded by a clear space, are present in mesentery of rats following transplantation of E28 pig pancreatic primordia. To ascertain whether similar cells are present in kidneys of rats transplanted with E28 pig pancreatic primordia and subsequently with porcine islets, we performed electron microscopy on tissue obtained 4 weeks after islet transplantation. Shown in FIG. 8A (arrow) is a cell in the renal subcapsular space with β cell morphology (containing granules (250-400 nm) which have a crystalline core surrounded by a clear space). A renal tubule (T) is labeled. A mononuclear cell infiltrate in the renal subcapsular space consists predominantly of macrophages. Two are labeled (arrowheads). FIG. 8B is a high-power view of two others. FIG. 8C shows a high power view of the granules with a crystalline core surrounded by a clear space.

It has been proposed that rejection of an islet cell xenograft is dependent on two different cellular mechanisms (see Korsgren 1997 Xenotransplantation 4, 11-19). The first is recognition of pig MHC molecules by cytotoxic lymphocytes via both direct and indirect pathways of antigen recognition, as occurs following rejection of an allograft. The second is an immune response characterized by T cell dependent infiltration of macrophages with histopathological characteristics of delayed-type hypersensitivity. The presence of macrophages beneath the renal capsule of rats transplanted with porcine islets subsequent to E28 pig pancreatic primordia (see e.g., FIG. 8) may reflect the second cellular mechanism in the context of engraftment of a cell component of porcine islets to which rats have been rendered tolerant by prior transplantation of E28 pig pancreatic primordia. Alternatively, since porcine islets are rejected by immune competent rats without prior transplantation of E28 pig pancreatic primordia the macrophages may represent a population of M2 phenotype (see Porta et al. 2009 Proc Natl Acad Sci USA 106, 14978-83) partially responsible for the observed tolerance.

Figure 9:
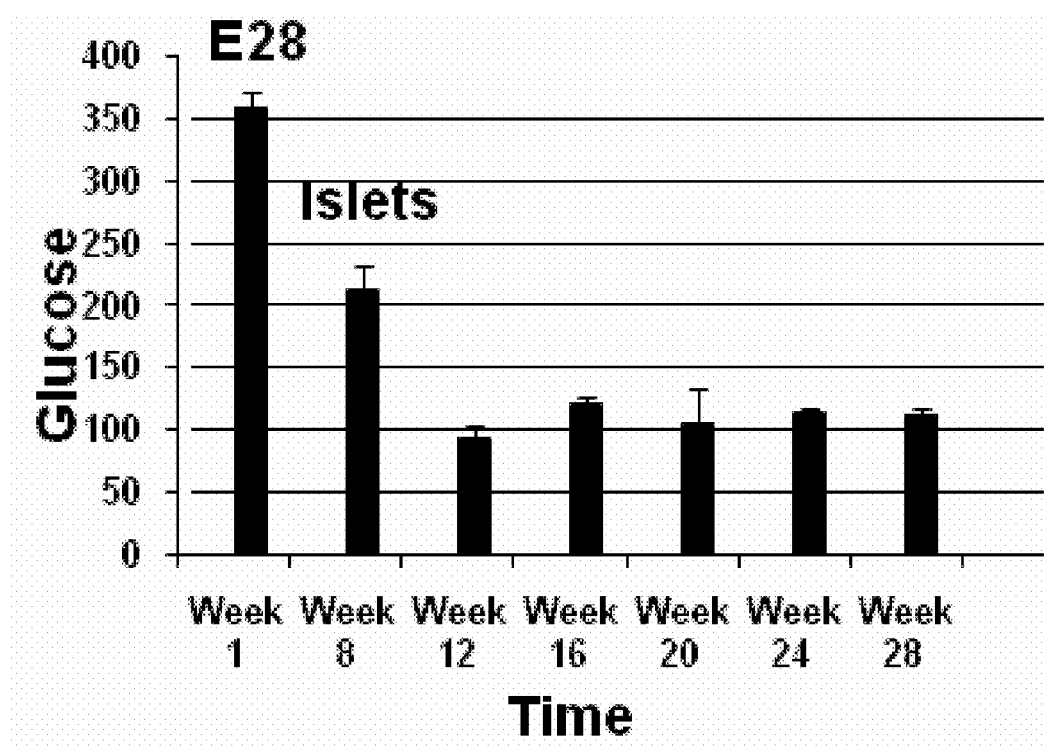
FIG. 9 is a bar graph showing Levels of fasting glucose measured over time in STZ diabetic rats transplanted with E28 pig pancreatic primordia (E28) after measurements on week 1 and implanted with porcine islets (islets) after measurements on week 8. Data are mean+/−SE of n=4 rats (weeks 1-12) or n=2 rats (weeks 16-28).

FIG. 9 shows levels of fasting glucose measured over time in STZ diabetic rats transplanted with E28 pig pancreatic primordia (E28) after measurements on week 1 and implanted with porcine islets (islets) after measurements on week 8 (Diab-E28-Islets group). Glucose levels were reduced to normal on week 12 (4 weeks following transplantation of islets) and remained so for 16 weeks thereafter (week 28).

Figure 10:
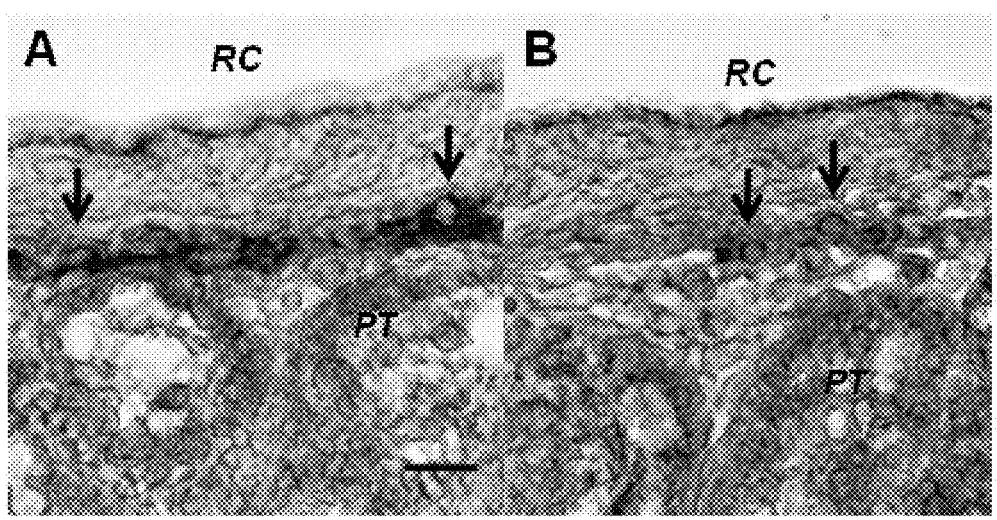
FIG. 10 is a series of Photomicrographs of kidney from a diabetic rat into which embryonic pig pancreas had been transplanted in mesentery and pig islets had been transplanted subsequently in kidney stained using anti-insulin antibody (FIG. 10A) or control antibody (FIG. 10B). Tissue was obtained 20 weeks after islet transplantation. Arrows delineate cells in the subcapsular space with β cell morphology. RC, renal capsule; PT, FIG. 10A and FIG. 10B. Scale bar: 10 µm (FIG. 10A).

FIG. 10 shows sections from a kidney of one of the rats from the Diab-E28-Islets group euthanized on week 28 (20 weeks following islet implantation). Sections are stained using anti-insulin antibodies (FIG. 10A) or control serum (FIG. 10B). Cells that stain for insulin (FIG. 10A, arrows) but not with control serum (FIG. 10B, arrows) are present in an expanded subcapsular space. The cells that stain positive for insulin (red-brown stain) are polygonal with round nuclei and abundant cytoplasm (arrow), a β cell morphology.

It has been proposed (see Hammerman 2009 Transplant Immunology 21, 93-100) that transplantation of E28 pig pancreatic primordia in the mesentery and migration of cells to mesenteric lymph nodes and liver recapitulates events that occur during induction of oral tolerance (see Macpherson et al. 2006 J Experimental Medicine 203, 497-500; Crispe et al. 2003 Nature Reviews Immunology 3, 51-62; Worbs et al. 2006 J Experimental Medicine 203, 519-527), the induction of which is dependent on antigen transport via afferent lymphatics into the draining mesenteric lymph nodes (see Worbs et al. 2006 J Experimental Medicine 203, 519-527). In effect, it is suggested that heterotopic introduction of embryonic pig pancreas in rat or primate mesentery coopts the function of the gut associated lymphoid tissues (GALT) a complex, redundant (see Macpherson et al. 2006 J Experimental Medicine 203, 497-500; Crispe et al. 2003 Nature Reviews Immunology 3, 51-62; Worbs et al. 2006 J Experimental Medicine 203, 519-527) and phylogenetically ancient system (see Matsunaga and Rahman 2001 Scand J Immunol 53, 1-6; Youson and Al-Mahrouki 1999 General and Comparative Endocrinology 116, 303-335) of which embryonic pancreas is a part (see Jansen et al. 1993 Autoimmunity 15, 31-38), that under normal conditions induces peripheral tolerance to ingested antigens in jawed vertebrates and their descendants. GALT may have served similarly to prevent an immune response to insulin-producing cells scattered originally in the gut epithelium of primitive vertebrates ((see Matsunaga and Rahman 2001 Scand J Immunol 53, 1-6; Youson and Al-Mahrouki 1999 General and Comparative Endocrinology 116, 303-335) and has been proposed to induce tolerance or immune suppression towards islet cell antigens during normal embryonic development (see Jansen et al. 1993 Autoimmunity 15, 31-38). Developmentally controlled lymphogenesis establishes a preferential trafficking route from the gut to pancreatic lymph nodes, a GALT component, in which T cells can be activated by antigens drained from the peritoneum and the gastrointestinal tract. Intestinal stress modifies the presentation of pancreatic self-antigens in pancreatic lymph nodes. The convergence of endocrine and intestinal contents at this site may explain the link between an autoimmune pathogenesis for type 1 diabetes and environmental provocation (see Jansen et al. 1993 Autoimmunity 15, 31-38; Turley et al. 2005 Proc Natl Acad Sci USA 102, 17729-17733).

Example 9

Implantation of Pig Pancreatic Primordia into Primates

This example demonstrates normalizing glucose in non-immune suppressed diabetic rhesus macaques via transplantation of pig pancreatic primordia followed by porcine islets. In effect, the "tolerance" induced by pig pancreatic primordia transplantation in diabetic rhesus macaques (as defined by prolonged engraftment of porcine tissue in non-immune suppressed primates) is used to enable subsequent implantation of islets from mature pigs without the need for host immune suppression.

Unless otherwise indicated, methods are according to Examples 1-8.

Figure 11:
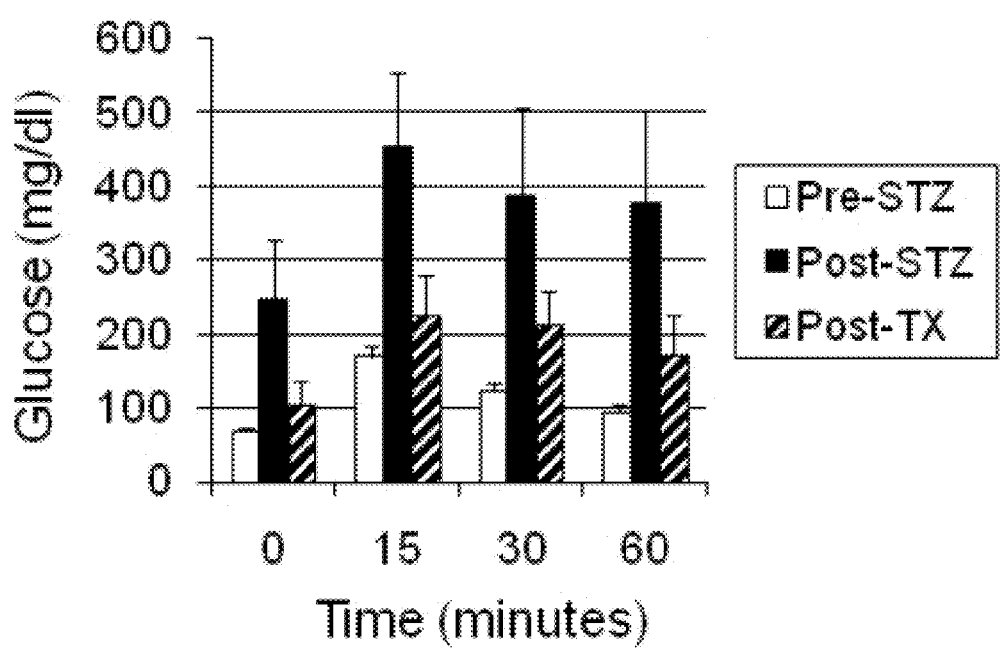
FIG. 11 is a bar graph showing Intravenous glucose tolerance in rhesus macaques. Glucose in peripheral venous blood was measured prior to intravenous infusion of 0.5 g/kg over 30 seconds as 50% dextrose (Time 0) and at several times after infusion in three fasted rhesus macaques either prior to administration of 60-140 mg/kg intravenous STZ (Pre-STZ); 5 days following administration of STZ (Post STZ); or 3 months following transplantation of 20-40 E28 pig pancreatic primordia in mesentery of STZ-diabetic macaques (Post-TX). Data are shown as mean±SE (3 macaques).

Intravenous glucose infusion was performed prior to administration of STZ to three fasted rhesus macaques (Pre-STZ); 5 days following administration of STZ (Post STZ) and 3 months following transplantation of 20-40 E28 pig pancreatic primordia in mesentery (Post-TX). The results are shown in FIG. 11. Levels measured at 60 minutes after intravenous glucose administration were not different from levels measured at Time 0 in Pre-STZ or Post-TX groups (Bonferroni Multiple Comparisons Test, P<0.05, two tailed analysis (GraphPad Instat 3, San Diego Calif.)). In contrast, levels measured at 60 minutes after intravenous glucose infusion were elevated relative to those measured at Time 0 in the Post-STZ group. Thus glucose tolerance is significantly improved post-transplantation of E28 pig pancreatic primordia in STZ-diabetic rhesus macaques.

Figure 12:
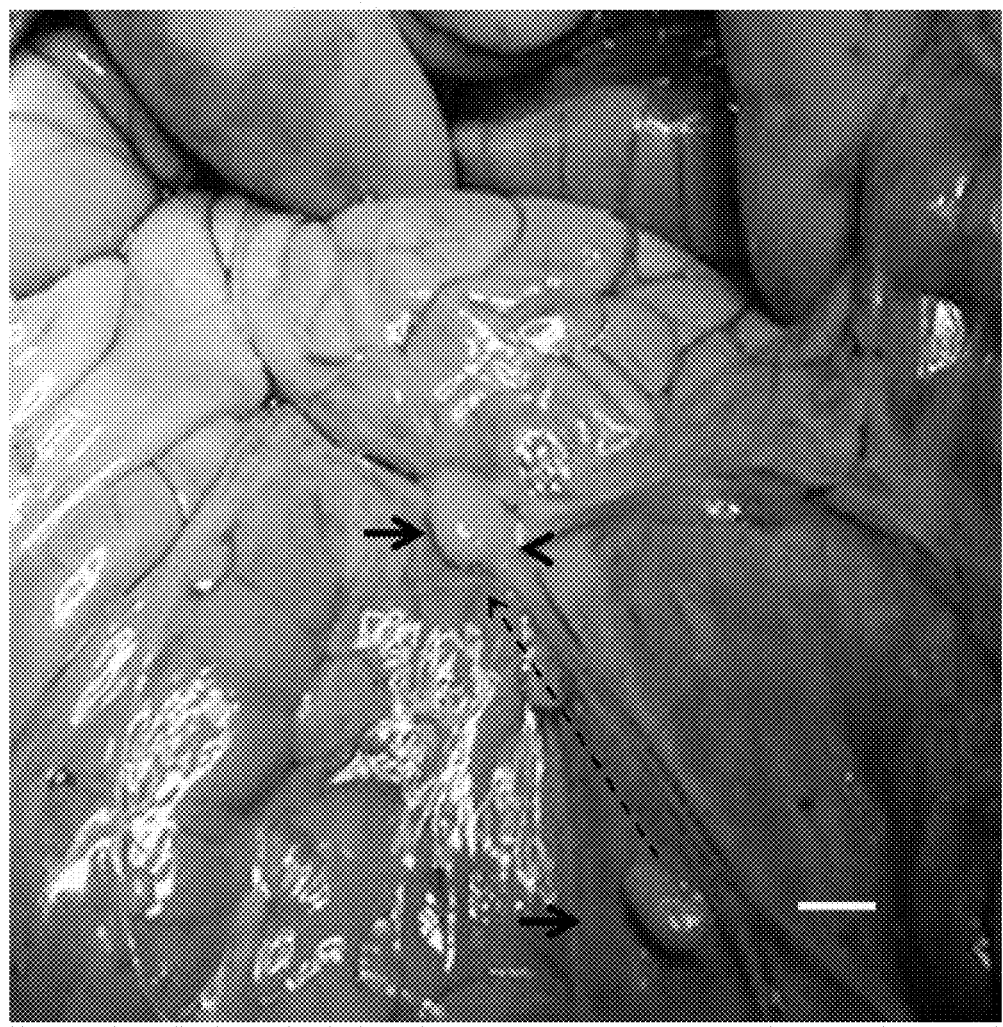
FIG. 12 is a photograph showing mesentery from a STZ-diabetic rhesus macaque transplanted previously with embryonic pig pancreas in mesentery and subsequently with pig islets in the left kidney. Enlarged lymph nodes in mesentery are delineated by arrows. The course of a lymphatic vessel is shown by a broken line with an arrowhead tip and the insertion of the lymphatic into a lymph node is delineated by a large arrowhead.

FIG. 12 shows mesentery from a STZ-diabetic rhesus macaque transplanted previously with embryonic pig pancreas in mesentery and subsequently with pig islets in the left kidney. Enlarged lymph nodes in mesentery are delineated by arrows. The course of a lymphatic vessel is shown by a broken line with an arrowhead tip and the insertion of the lymphatic into a lymph node is delineated by a large arrowhead.

Figure 13:
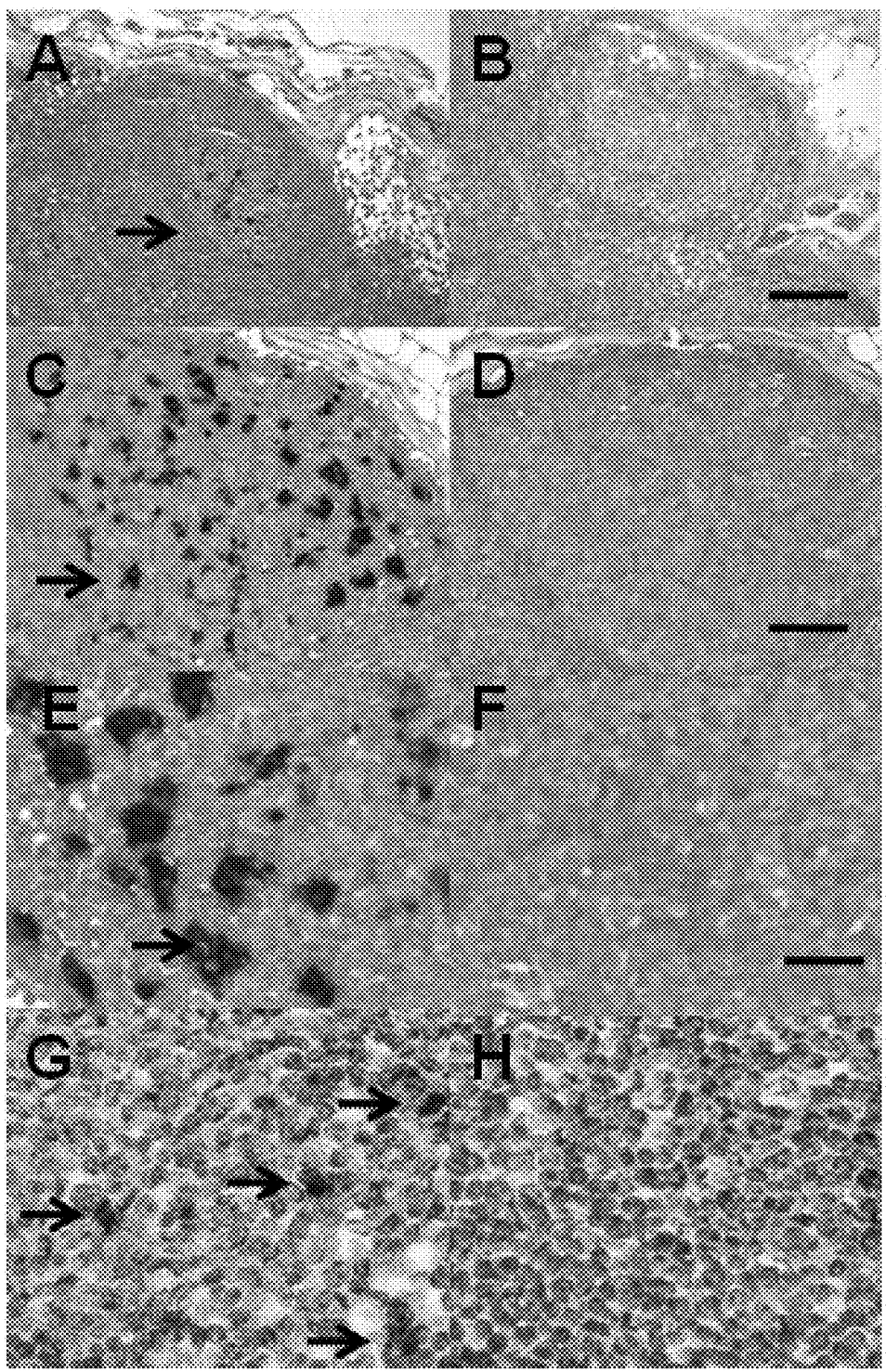
FIG. 13 is a series images showing sections from a mesenteric lymph node from a STZ-diabetic rhesus macaque transplanted previously with embryonic pig pancreas in mesentery and subsequently with pig islets in the left kidney: stained using anti-insulin antibodies (FIG. 13A,C,E) or control antiserum (FIG. 13B,D,F); or hybridized to an antisense (FIG. 13G) or sense (FIG. 13H) probe for porcine proinsulin mRNA. Scale bars: 80 µm (FIG. 13A and FIG. 13B), 25 µm (FIG. 13C and FIG. 13D), or 15 µm (FIG. 13E and FIG. 13F).

FIG. 13 shows sections from a mesenteric lymph node from a STZ-diabetic rhesus macaque transplanted previously with embryonic pig pancreas in mesentery and subsequently with pig islets in the left kidney: stained using anti-insulin antibodies (FIG. 13A,C,E) or control antiserum (FIG. 13B, D,F); or hybridized to an antisense (FIG. 13G) or sense (FIG. 13H) probe for porcine proinsulin mRNA. As before in macaques transplanted only with pig pancreatic primordia (15) cells are present with beta cell morphology that stain for insulin (FIG. 13A,C,E arrows) and to which the antisense porcine proinsulin mRNA probe anneals (FIG. 13G arrows). No staining for insulin is observed in sections incubated with control antiserum (FIG. 13B,D, F). No hybridization is observed if a sense probe is substituted for the antisense probe (FIG. 13H).

Figure 14:
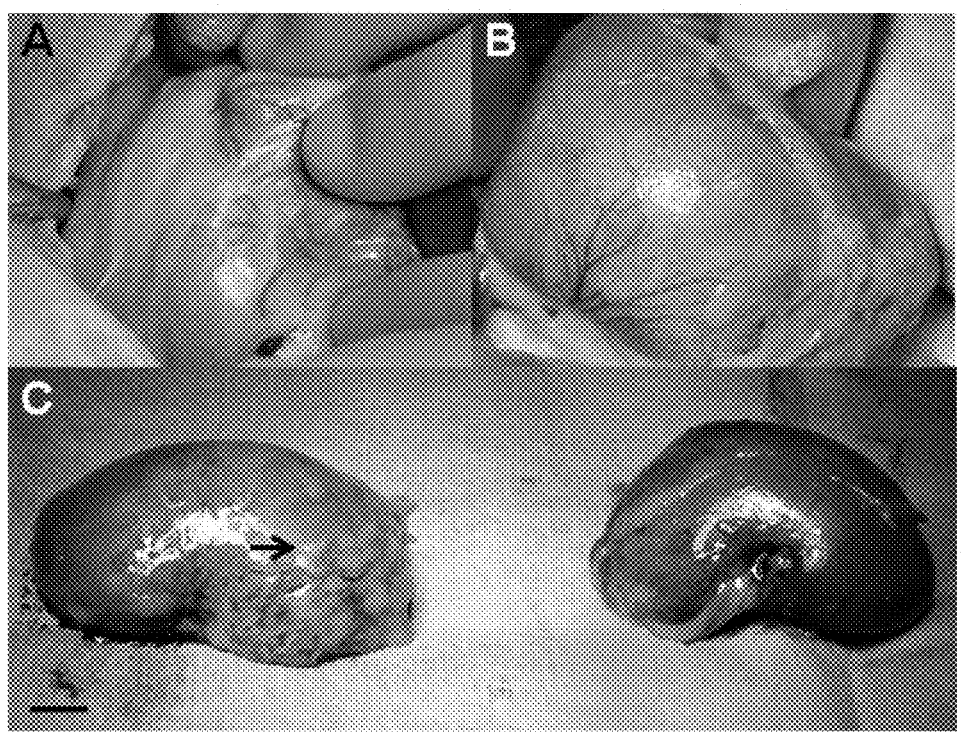
FIG. 14 is a series of images showing the kidneys from a STZ-diabetic rhesus macaque transplanted previously with embryonic pig pancreas in mesentery and subsequently with pig islets in the left kidney.

FIG. 14 shows the kidneys from a STZ-diabetic rhesus macaque transplanted previously with embryonic pig pancreas in mesentery and subsequently with pig islets in the left kidney. FIG. 14A shows the left kidney prior to retraction of the retroperitoneal membrane. FIG. 14B shows the left kidney after retraction of the retroperitoneal membrane. FIG. 14C shows the left kidney (left) and the right kidney (right) after removal from the rhesus macaque. Grossly, left and right kidneys appear identical with the exception of increased capsular fat (arrow) on the left kidney.

Figure 15:
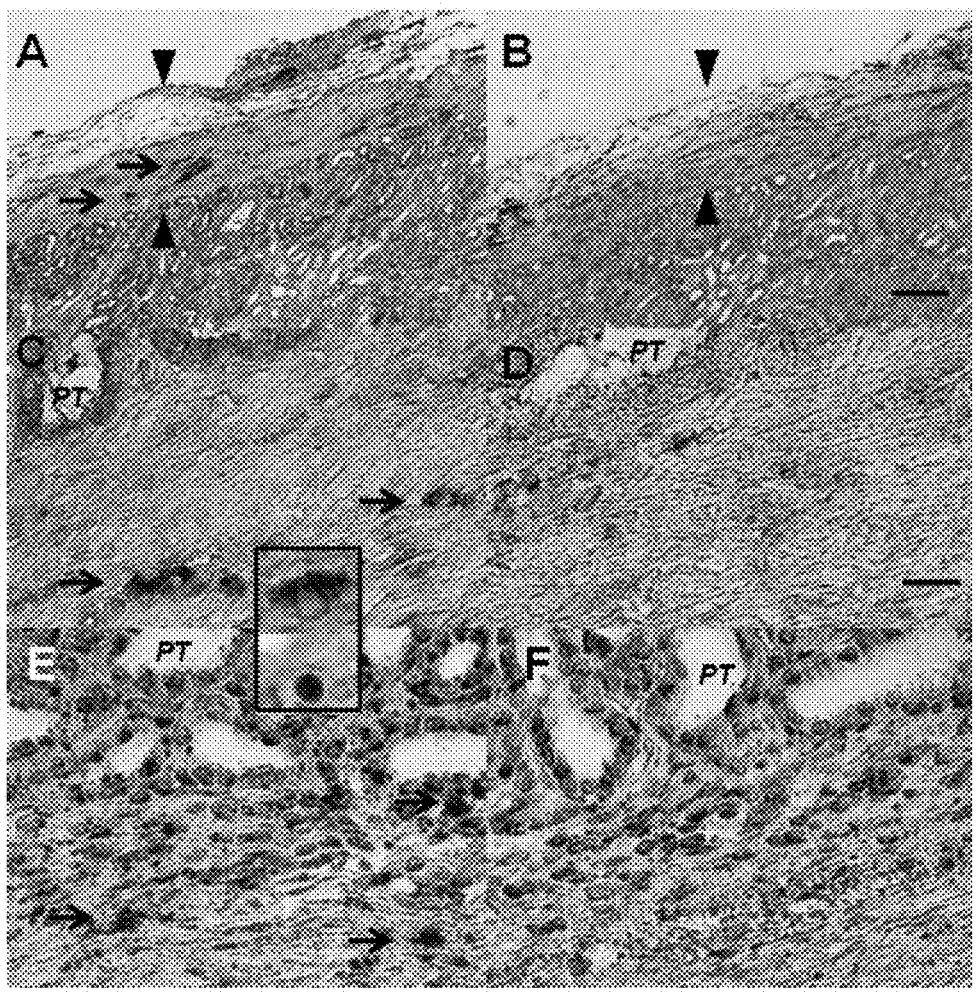
FIG. 15 is a series of images showing sections from the left kidney from a STZ-diabetic rhesus macaque transplanted previously with embryonic pig pancreas in mesentery and subsequently with pig islets in the left kidney. Sections are stained using anti-insulin antibodies (FIG. 15A, C) or control serum (FIG. 15 B, D); or hybridized to an antisense (FIG. 15E) or sense (FIG. 15F) probe for porcine proinsulin mRNA. Cells that stain for insulin (FIG. 15A, C arrows) are present in the subcapsular space (arrowheads). Scale bars: 80 um (FIG. 15A and FIG. 15B), 10 um (FIG. 15 C, FIG. 15D, FIG. 15E and FIG. 15F).

FIG. 15 shows sections from the left kidney from a STZ-diabetic rhesus macaque transplanted previously with embryonic pig pancreas in mesentery and subsequently with pig islets in the left kidney. Sections are stained using anti-insulin antibodies (FIG. 15A, C) or control serum (FIG. 15 B, D); or hybridized to an antisense (FIG. 15E) or sense (FIG. 15F) probe for porcine proinsulin mRNA. Cells that stain for insulin (FIG. 15 A, C arrows) are present in the subcapsular space (arrowheads). The cells that stain positive for insulin (red-brown stain) are polygonal with round nuclei and abundant cytoplasm (arrow), a beta cell morphology (Rogers et al. 2007 Xenotransplantation 14, 591-602). Cells are present in the subcapsular space to which the antisense porcine proinsulin mRNA probe binds (FIG. 15E arrows). No staining for insulin is observed in sections incubated with control antiserum (FIG. 15B,D). No hybridization is observed if a sense probe is substituted for the antisense probe (FIG. 15F). PT, proximal tubule. Insets (C and E respectively) show high power views of insulin staining and hybridization with porcine proinsulin mRNA antisense probe.

Figure 16:
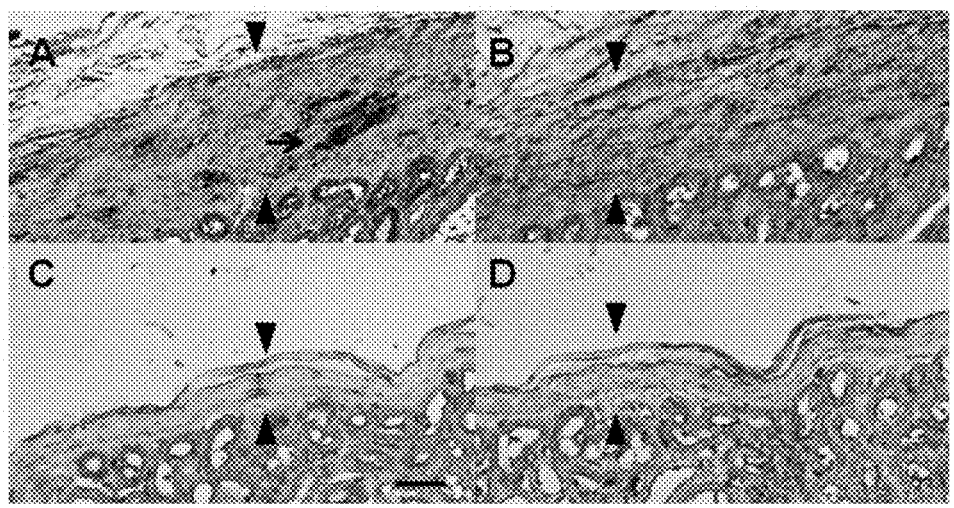
FIG. 16 is a series of images showing sections from the left kidney (FIG. 16 A,B) or the right kidney (FIG. 16 C,D) from a STZ-diabetic rhesus macaque transplanted previously with embryonic pig pancreas in mesentery and subsequently with pig islets in the left kidney. Sections are stained using anti-insulin antibodies (FIG. 16A, C) or control serum (FIG. 16 B, D). Scale bar: 80 um (FIG. 16A, FIG. 16B, FIG. 16C and FIG. 16D).

FIG. 16 shows sections from the left kidney (FIG. 16 A,B) or the right kidney (FIG. 16 C,D) from a STZ-diabetic rhesus macaque transplanted previously with embryonic pig pancreas in mesentery and subsequently with pig islets in the left kidney. Sections are stained using anti-insulin antibodies (FIG. 16 A, C) or control serum (FIG. 16 B, D). Cells that stain for insulin (FIG. 16 A arrow), but not with control serum (FIG. 16 B) are present in a subcapsular space (arrowheads) that is expanded in the left kidney (FIG. 16 A,B) relative to the right kidney (FIG. 16 C,D).

Figure 17:
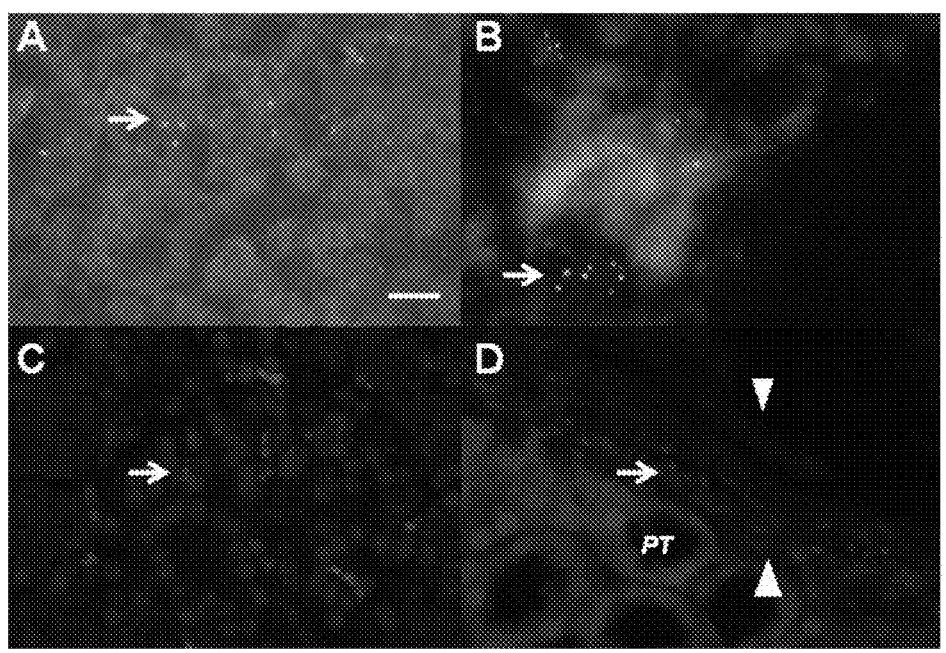
FIG. 17 is a series of images showing fluorescent in-situ hybridization performed using probes specific for the pig X chromosome (FIG. 17 right).

The antisense probe for porcine proinsulin mRNA is specific for pig (FIG. 15). To provide additional evidence that cells in mesenteric lymph nodes and the left kidney of the macaque transplanted with pig pancreatic primordia and subsequently with porcine islets originate from pig, fluorescent in-situ hybridization was performed using probes specific for the pig X chromosome (FIG. 17). Shown in FIGS. 17 A and C are pig X chromosomes in nuclei of cells from a normal porcine pancreas (arrow positive controls) stained using two different probes (green A; pink C). FIGS. 17 B and D (arrows) show pig X chromosomes in the nuclei of cells in the mesenteric lymph node (FIG. 17B) and renal subcapsular space (D arrowheads).

Figure 18:
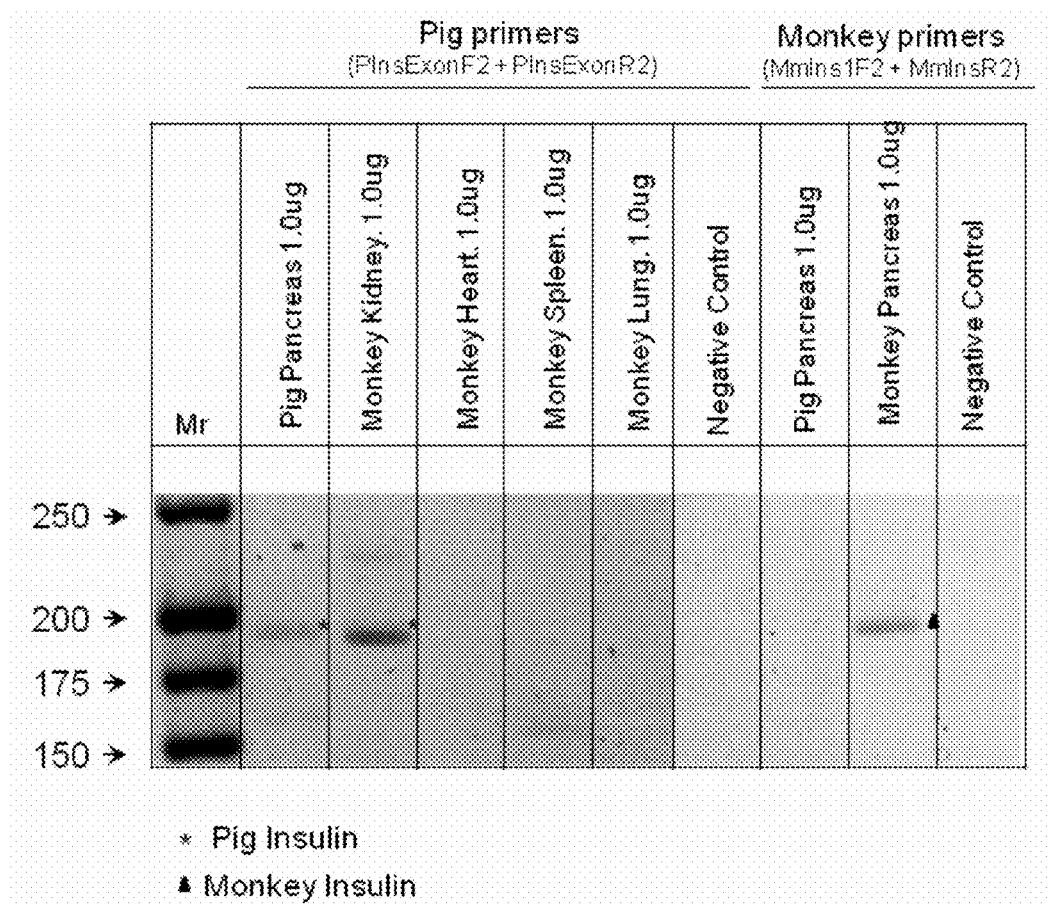
FIG. 18 is an image of a gel showing RT-PCR analysis of purified RNA from homogenized organ tissue excised from a macaque transplanted with E28 pig pancreatic primordia in mesentery and subsequently with porcine islets in the left renal subcapsular space. RT-PCR performed using intron-spanning primers for proinsulin mRNA to eliminate the possibility of false amplification from genomic DNA. Products were sequenced to confirm identities. The pig primers amplify a band of 193 bps in RNA originating from pig pancreas, corresponding to pig proinsulin insulin mRNA. The rhesus macaque (monkey) primers amplify a band of 199 bps corresponding to monkey proinsulin insulin mRNA in monkey pancreas. Pig proinsulin mRNA is also detected in monkey kidney.
Figure 19:
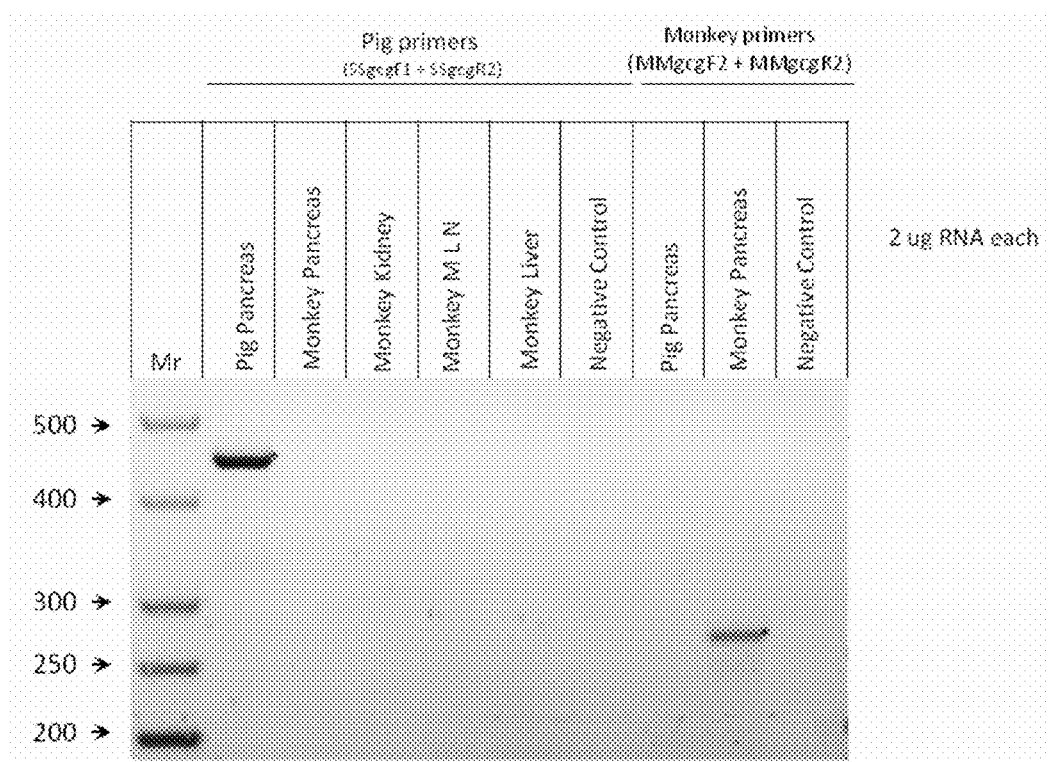
FIG. 19 is an image of a gel showing RT-PCR performed using intron-spanning primers for pig or monkey pro glucagon mRNA that is expressed in alpha cells within islets. The pig primers amplify a band of 448 bps in RNA originating from pig pancreas, corresponding to pig glucagon mRNA. The rhesus macaque primers amplify a band of 263 bps corresponding to monkey glucagon mRNA in monkey pancreas RNA. No pig glucagon can be detected in any tissues from the transplanted rhesus macaque.

Multiple organs were excised from a macaque transplanted with E28 pig pancreatic primordia in mesentery and subsequently with porcine islets in the left renal subcapsular space. Tissues were homogenized individually and total RNA was purified. RT-PCR was performed using intron-spanning primers for proinsulin mRNA to eliminate the possibility of false amplification from genomic DNA. Results are shown in FIG. 18. Products were sequenced to confirm identities. The pig primers amplify a band of 193 bps in RNA originating from pig pancreas, corresponding to pig proinsulin insulin mRNA. The rhesus macaque (monkey) primers amplify a band of 199 bps corresponding to monkey proinsulin insulin mRNA in monkey pancreas. Pig proinsulin mRNA is also detected in monkey kidney.

To ascertain whether non-beta cell components originating from pig pancreatic primordia or porcine islets engraft in rhesus macaques transplanted with E28 pig pancreatic primordia in mesentery and subsequently with porcine islets in the left renal subcapsular space, RT-PCR was performed using intron-spanning primers for pig or monkey pro glucagon mRNA that is expressed in alpha cells within islets.

The pig primers amplify a band of 448 bps in RNA originating from pig pancreas, corresponding to pig glucagon mRNA (see FIG. 9). The rhesus macaque primers amplify a band of 263 bps corresponding to monkey glucagon mRNA in monkey pancreas RNA. But unlike the case for porcine proinsulin mRNA that can be detected in lymph nodes and liver from macaques following transplantation of E28 pig pancreatic primordia (Rogers et al. 2007 Xenotransplantation 14, 591-602) or in kidney from rhesus macaques transplanted with E28 pig pancreatic primordia and porcine islets (see FIG. 8), no pig glucagon can be detected in any tissues from the transplanted rhesus macaque. The data suggest that alpha cells originating from pig pancreatic primordia or porcine islets do not engraft following transplantation of the tissues in rhesus macaques.

The above example demonstrates engraftment of porcine islets in non-immune suppressed macaques rendered tolerant by prior transplantation of embryonic pig pancreas and, as such, supports that comparable engraftment will occur in humans with diabetes mellitus. The ability to employ porcine islet transplants to normalize glucose tolerance in non-immune suppressed human subjects would widen the applicability for and reduce the toxicity of transplantation therapy for diabetes mellitus.

Example 10

Experimental Design for Primate Transplant Studies

Induction of diabetes mellitus and treatment with exogenous insulin.

Insulin-dependent diabetes mellitus will be induced in prepubescent (2.5-3.5 kg) male rhesus (Rh) macaques (Maccaca mullata) obtained from Southwest Foundation for Biomedical Research, San Antonio Tex. via bolus injection of 60-125 mg/kg STZ, a dose recognized to produce diabetes reliably in rhesus macaques (Rogers et al. 2007 Xenotransplantation 14, 591-602). Beginning immediately after STZ administration, blood glucose will be monitored twice daily, levels recorded and insulin administered (two daily Lantus insulin injections plus 1-2 units of Lispro as needed (Rogers et al. 2007 Xenotransplantation 14, 591-602)) in order to maintain glucose levels at or below 200 mg/dl. All insulin will be discontinued if levels are persistently less than 200 mg/dl. Macaques will have free access to water and will be fed Harlan 2050 Teklad Global 20% protein diet supplemented with fresh fruit (3.5% of their body weight per day) divided in 2 meals, each after glucose measurements and administration of insulin.

Isolation and Transplantation of Pancreatic Primordia.

At 28 days gestation, pregnant Yorkshire pigs (Oak Hill Genetics, Ewing Ill.) will be intubated and anesthesia maintained by inhalation of isoflurane and $O_2$ to effect. The uterus will be removed and the donor pig then euthanized. Pancreatic primordia from E28 pig embryos will be surgically isolated under a dissecting microscope. After isolation, primordia will be placed immediately into an ice-cold Dulbecco's modified Eagles Medium: Hams F12 (DMEM:HF12) solution containing transferring, prostaglandin E1 and growth factors as described (Rogers et al. 2007 Xenotransplantation 14, 591-602). After 45 minutes, pancreatic primordia will be implanted between layers of mesentery in non-immune suppressed rhesus macaques exactly as in previous studies (Rogers et al. 2007 Xenotransplantation 14, 591-602).

Isolation and Implantation of Porcine Islets

Porcine islets of Langerhans will be isolated from female Yorkshire pigs exactly as in previous studies (Rogers et al. 2007 Xenotransplantation 14, 591-602). Alternatively, islets will be isolated from Large White domestic pigs transgenic for GFP (Whitworth et al. 2009 Molecular Reproduction & Development 76, 490-500).

A number of islets sufficient to normalize blood glucose levels when transplanted beneath the renal capsule of diabetic non-human primates (15,000 to 20,000 IEQ per kg (Dufrane et al. 2006 Transplantation 81, 1345-1353; Komoda et al. 2005 Xenotransplantation 12, 209-216)) will be transplanted beneath the renal capsule of rhesus macaques. Macaques will be sedated with 10-15 mg/kg intramuscular (im) ketamine and mask induced with isoflurane. An appropriately sized endrotracheal tube will be placed & animals will be maintained under isoflurane anesthesia for the duration of the surgical procedure. Anesthesia monitoring will include pulse oximetry, capnography, electrocardiography, blood pressure measurements, core body temperature as well as monitoring for adequate anesthesia depth, absence of spontaneous movement, lack of response to pain and stable physiologic parameters. Anesthesia will be adjusted as needed depending on parameters being monitored. The animal will be prepared for surgery and a midline abdominal incision and the left kidney exposed. A small tear will be made into the capsule with a fine forceps and a 22G cathether slipped under the capsule. Islets will be slowly released under the capsule by a 1 cc syringe attached to the catheter. Once the islets have been implanted and the tear repaired the catheter will be removed and the animal will be closed. Unless otherwise noted, rhesus macaques will have been transplanted in mesentery with E28 pig pancreatic primordia 3-4 months previously. If the portal vein is used as the islet infusion site, the portal vein will be isolated and the islets will be injected into the vein using a 1 cc syringe with an appropriately sized needle.

Glucose, and Insulin Measurements, IV GTT (Intravenous Glucose Tolerance Test).

Levels of glucose will be measured using the Hemocue B-glucose Analyzer (Hemocue, Lake Forest Calif.) in whole blood. IV GTT: Exogenous insulin will be held for 24 hours in rhesus macaques fasted for 18 hours prior to administration of glucose (0.5 g/kg) intravenously over 30 seconds as 50% dextrose. Peripheral venous blood samples will be taken prior to injection (Time 0) and at several times after administration. Analysis of intact insulins will be performed using immunoaffinity chromatography HPLC and mass spectrometry. Immunoaffinity chromatography will be carried out using an Agilent 1100 Series high performance liquid chromatography (Palo Alto, Calif.) interfaced to an Applied Biosystems QTrap 4000 mass spectrometer (Foster City, Calif.). Anti-insulin immunoaffinity gel will be obtained from CER, (Marloie Belgium). The mass spectrometer will be operated in the positive mode at an ion spray voltage of 5500 V, and the declustering potential will be optimized for efficient isolation of the 5-fold protonated molecules of human insulin (m/z 1162.4) and porcine insulin (m/z 1156.3) (Rogers et al. 2007 Xenotransplantation 14, 591-602).

Histology.

Tissues will be fixed in 10% formalin (Rogers et al. 2007 Xenotransplantation 14, 591-602) following removal from hosts. The fixative will be removed, and tissues embedded in paraffin, sliced into 5-10 um sections and placed on glass slides in preparation for staining. Polyclonal rabbit anti-insulin serum (Accurate Chemicals; Westbury N.Y.) will be used to detect insulin in tissue sections. Non-immune rabbit serum will be substituted for control stains (Rogers et al. 2007 Xenotransplantation 14, 591-602). Sections will be counterstained using hematoxylin.

Detection of Insulin Transcripts Using RT-PCR or In-Situ Hybridization.

Tissues will be excised from the rhesus macaque and frozen immediately. Tissues will be homogenized individually and total RNA purified using RNeasy Mini kit (QIAGEN, CA, USA). DNase in-column digestion will be carried out to eliminate DNA from the RNA samples. For RT-PCR, the Invitrogen Superscript One-Step RT-PCR kit (Invitrogen, CA, USA) will be used. The reactions will be carried out in a MJ research thermal cycler (MJ Research, Mass., USA). For the specific amplification of pig insulin transcripts (GenBank: AY044828), the primers used are: SsInsF2: 5'-AACCCT-CAGGCAGGTGCC-3' (SEQ ID NO: 2); SsInsR2: 5'-GGGGTGCGGGGAGCAGCA-3' (SEQ ID NO: 3), using conditions: 30 minutes at 55 degrees C., 2 minutes at 94 degrees C., and followed by 40 cycles of 94 degrees C., 15"; 64 degrees C., 30"; 68 degrees C., 25". For monkey insulin transcripts (Human Genome Sequencing Center Baylor College of Medicine: Contigs 422635 and 421061), the primers used are: MmIns1F2: 5'-GACCCTCAGGTGGGGCAG-3' (SEQ ID NO: 4); MmInsR2: 5"-AGGAGGCGGAGGGT-GTGG-3' (SEQ ID NO: 5) using conditions: 30 minutes at 55 degrees C., 2 minutes at 94 degrees C., and followed by 40 cycles of 94 degrees C., 15"; 61 degrees C., 35"; 68 degrees C., 25". All products will be separated by electrophoresis on 3% agarose gels and their identities were confirmed by sequencing. The primers are intron-spanning to eliminate the possibility of false amplification from genomic DNA. The pig primers amplify a band of 193 bps in RNA originating from pig pancreas, corresponding to pig insulin mRNA. The monkey primers amplify a band of 199 bps corresponding to monkey insulin mRNA in monkey pancreas RNA.

For the specific amplification of pig pro glucagon transcripts (GenBank: AY609582.1), the primers used are: SSgcgF1: 5'-ccccaactctgttccgac-3 (SEQ ID NO: 6); SSgcgR2: 5'-TTCGACAATGGTAACTTCC-3' (SEQ ID NO: 7), using conditions: 30 minutes at 55 degrees C., 2 minutes at 94 degrees C., and followed by 40 cycles of 94 degrees C., 20"; 55 degrees C., 45"; 68 degrees C., 25". For monkey glucagon transcripts (GenBank: XM_001093871.1), the primers used are: MMgcgF2: 5'-CATTCACAGGGCACATTC-3' (SEQ ID NO: 8); MMgcgR2: 5"-TTCAACAATGGCGACCTCT-3' (SEQ ID NO: 9) using conditions: 30 minutes at 55 degrees C., 2 minutes at 94 degrees C., and followed by 40 cycles of 94 degrees C., 20"; 60 degrees C., 45"; 68 degrees C., 25". All products will be separated by electrophoresis on 3% agarose gels and their identities were confirmed by sequencing. The primers are intron-spanning to eliminate the possibility of false amplification from genomic DNA. The pig primers amplify a band of 448 bps in RNA originating from pig pancreas, corresponding to pig pro glucagon mRNA and the monkey primers amplify a band of 263 bps corresponding to monkey pro glucagon mRNA in monkey pancreas RNA.

In situ hybridization will be performed on 5 um paraffin-embedded sections using digoxin-labeled antisense probes for porcine proinsulin mRNA (Rogers et al. 2007 Xenotransplantation 14, 591-602). A sense probe will be used for control stains.

Fluorescent In-Situ Hybridization.

Fluorescence in situ hybridization in paraffin-embedded tissue sections will be performed exactly as in Rogers 2010 (Am. J. Pathology 177, 854-864) and visualized using an Olympus BX61 epifluorescence microscope system with software that enables generation of composite images obtained using multichannel monochrome captures.

Electron Microscopy:

Electron microscopy will be performed as in before Rogers et al. 2007 Xenotransplantation 14, 591-602. Fresh tissue will be fixed initially in 3% (wt/vol) glutaraldehyde buffer and post-fixed in OsO4. Samples will be dehydrated in ETOH and embedded in poly/bed 812 resin (Poly Science, Inc, Warrington, Pa.). Thin sections will be prepared and stained with uranyl acetate and lead citrate are examined using a Phillips Morgani model transmission electron microscope.

Example 11

Long-Term Engraftment of a Cell Component of Porcine Islets in STZ-Diabetic Rhesus Macaques Transplanted Previously with E28 Pig Pancreatic Primordia Unless otherwise indicated, methods are according to Example 10.

STZ-diabetic rhesus macaques will be transplanted in mesentery with E28 pig pancreatic primordia and 1 month later will be implanted with porcine islets in the renal subcapsular space of one kidney. It is expected that requirements for exogenous insulin will be reduced following transplantation of E28 pig pancreatic primordia and glucose tolerance will be improved (see e.g., FIG. 11), but that macaque will continue to require exogenous insulin to maintain euglycemia.

Six weeks following implantation of porcine islets, the macaque will be euthanized. Engraftment of pig tissue in the mesenteric lymph node and kidney of primates will be documented using immune histochemistry for insulin; RT-PCR and in-situ hybridization for porcine proinsulin mRNA; electron microscopy; and Fluorescent in-situ hybridization for the porcine X chromosome. Control experiments will examine tissue from STZ-diabetic rhesus macaques into which islets are implanted in the renal subcapsular space without prior transplantation of E28 pig pancreatic primordia For initial experiments porcine islets will be implanted in kidney because pig beta cells originating from pancreatic primordia transplanted in mesentery do not engraft in kidney. Therefore, porcine endocrine tissue in kidney following implantation of islets in the renal subcapsular space need to originate from porcine islets. In subsequent experiments, porcine islets will be infused into the portal vein of STZ-diabetic rhesus macaques previously transplanted in mesentery with E28 pig pancreatic primordia. However, since pig cell originating from transplanted E28 pancreatic primordia engraft in liver following transplantation of E28 pig pancreatic primordia in mesentery, it may be difficult to establish the origin of cells originating from islets implanted via portal vein infusion. The method used to circumvent that difficulty will be to infuse islets from female pigs transgenic for green fluorescent protein (GFP) and track cells originating from transplanted islets using the GFP marker.

What is claimed is:

1. A method for treating diabetes mellitus in a subject in need thereof comprising:

implanting a porcine pancreatic primordium, or a portion thereof, in an amount effective to induce tolerance to porcine islet cells comprising mature antigen-presenting cells, into a non-porcine mammalian subject;

waiting a period of time sufficient to induce tolerance to porcine islet cells comprising mature antigen-presenting cells; and implanting porcine islet cells comprising mature antigen-presenting cells into the non-porcine mammalian subject.

2. The method of claim 1 wherein a requirement for immunosuppression is reduced or eliminated.

3. The method of claim 1, wherein the porcine pancreatic primordium is isolated about 7 days after formation of an embryonic pig pancreas.

4. The method of claim 1, wherein the developmental age of the porcine pancreatic primordium is at least about E27 but not more than about E35.

5. The method of claim 4, wherein the developmental age of the porcine pancreatic primordium is about E28.

6. The method of claim 1, wherein the pancreatic primordium comprises at least one embryonic dorsal, ventral, or fused pancreatic primordium that is substantially non-vascularized at the time of the harvest.

7. The method of claim 1, wherein the pancreatic primordium comprises at least one embryonic dorsal, ventral, or fused pancreatic primordium; and the pancreatic primordium is substantially free of antigen-presenting cells at the time of the harvest.

8. The method of claim 1, wherein at least about one pancreatic primordium, or an equivalent amount of portions of a pancreatic primordium sufficient to induce tolerance to porcine islet cells, are implanted into the subject.

9. The method of claim 8, wherein at least about 1 to about 20 pancreatic primordia, or an equivalent amount of portions of pancreatic primordia sufficient to induce tolerance to porcine islet cells, are implanted into the subject.

10. The method of claim 1, wherein the pancreatic primordia are implanted at one or more positions selected from the group consisting of: peritoneal cavity; mesentery; near the subject's omentum adjacent to a branch of the subject's superior mesenteric artery; into a pouch of the omentum; in the subject's kidney capsule; under the subject's kidney capsule; within skeletal muscle; and in the subcutaneous space.

11. The method of claim 1, wherein the period of time sufficient to induce tolerance to porcine islet cells is at least about 10 days after implantation of the porcine pancreatic primordia.

12. The method of claim 1, wherein the implanted porcine pancreatic primordia remains in place in the subject during the period of time sufficient to induce tolerance to porcine islet cells.

13. The method of claim 1, wherein the porcine islet cells are implanted into the subject in an amount of at least about 10,000 islet equivalents per kg of the subject.

14. The method of claim 1, wherein the porcine islet cells are implanted at one or more sites by intrahepatic islet infusion or intraportal injection.

15. The method of claim 1, wherein the porcine islet cells comprise at least one of: $\alpha$ cells; $\beta$ cells; $\delta$ cells; PP cells; and stem cells.

16. The method of claim 1, further comprising monitoring the subject for one or more of: implanted islet cell function; islet cell graft loss; insulin secretion, hematological and biochemical parameters; and plasma levels of porcine insulin.

17. The method of claim 1, wherein the mammalian subject is selected from the group consisting of: horse, cow, dog, cat, sheep, pig, mice, rat, monkey, guinea pig, chicken, and human.

18. The method of claim 17, wherein the mammalian subject is a human.

19. The method of claim 1, wherein the diabetes mellitus comprises at least one of: Type 1 diabetes, Type 2 diabetes, pre-diabetes, gestational diabetes, congenital diabetes due to genetic defects of insulin secretion, cystic fibrosis-related diabetes, steroid diabetes induced by high doses of glucocorticoids, and monogenic diabetes.

20. The method of claim 19, wherein the diabetes mellitus is Type 1 diabetes or Type 2 diabetes.

21. The method of claim 1, wherein the porcine islet cells are implanted at one or more sites selected from the group consisting of: in the peritoneal cavity; in subcutaneous tissue; and in the omentum of the subject.

22. The method of claim 1, wherein the porcine islet cells are implanted at one or more sites selected from the group consisting of: in the kidney capsule; underneath the kidney capsule; in epididymal fat; and in pancreas of the subject.

* * * * *

```
                         SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: probe for in situ hybridization

<400> SEQUENCE: 1
ggcggagaac cctcaggcag gtgccgtgga gctgg                              35

<210> SEQ ID NO 2
<211> LENGTH: 18
<212> TYPE: DNA
<213> ORGANISM: Artificial Sequence
<220> FEATURE:
<223> OTHER INFORMATION: SsInsF2 PCR primer

<400> SEQUENCE: 2
aaccctcagg caggtgcc                                                 18

<210> SEQ ID NO 3
<211> LENGTH: 18
<212> TYPE: DNA
<213> ORGANISM: Artificial Sequence
<220> FEATURE:
<223> OTHER INFORMATION: SsInsR2 PCR primer

<400> SEQUENCE: 3
ggggtgcggg gagcagca                                                 18

<210> SEQ ID NO 4
<211> LENGTH: 18
<212> TYPE: DNA
<213> ORGANISM: Artificial Sequence
<220> FEATURE:
<223> OTHER INFORMATION: MmIns1F2 PCR primer

<400> SEQUENCE: 4
gaccctcagg tggggcag                                                 18

<210> SEQ ID NO 5
<211> LENGTH: 18
<212> TYPE: DNA
<213> ORGANISM: Artificial Sequence
<220> FEATURE:
<223> OTHER INFORMATION: MmInsR2 PCR primer

<400> SEQUENCE: 5
aggaggcgga gggtgtgg                                                 18
```

```
<210> SEQ ID NO 6
<211> LENGTH: 18
<212> TYPE: DNA
<213> ORGANISM: Artificial Sequence
<220> FEATURE:
<223> OTHER INFORMATION: SSgcgF1 PCR primer

<400> SEQUENCE: 6
ccccaactct gttccgac                                              18

<210> SEQ ID NO 7
<211> LENGTH: 19
<212> TYPE: DNA
<213> ORGANISM: Artificial Sequence
<220> FEATURE:
<223> OTHER INFORMATION: SSgcgR2 PCR primer

<400> SEQUENCE: 7
ttcgacaatg gtaacttcc                                             19

<210> SEQ ID NO 8
<211> LENGTH: 18
<212> TYPE: DNA
<213> ORGANISM: Artificial Sequence
<220> FEATURE:
<223> OTHER INFORMATION: MMgcgF2 PCR primer

<400> SEQUENCE: 8
cattcacagg gcacattc                                              18

<210> SEQ ID NO 9
<211> LENGTH: 19
<212> TYPE: DNA
<213> ORGANISM: Artificial Sequence
<220> FEATURE:
<223> OTHER INFORMATION: MMgcgR2 PCR primer

<400> SEQUENCE: 9
ttcaacaatg gcgacctct                                             19
```